United States Patent [19]

Chalfie et al.

[11] Patent Number: 5,196,333
[45] Date of Patent: Mar. 23, 1993

[54] DNA SEQUENCES INVOLVED IN NEURONAL DEGENERATION, MULTICELLULAR ORGANISMS CONTAINING SAME AND USES THEREOF

[75] Inventors: Marin Chalfie, New York, N.Y.; Eve Wolinsky, Princeton, N.J.; Monica Driscoll, New York, N.Y.

[73] Assignee: The Trustees of Columbia University, New York, N.Y.

[21] Appl. No.: 530,968

[22] Filed: May 30, 1990

[51] Int. Cl.$^5$ .............. C12N 5/00; C07H 15/12; C12P 21/06; C12Q 1/68

[52] U.S. Cl. .............. 435/240.1; 435/29; 435/69.1; 435/70.3; 536/23.5; 935/1; 935/19; 935/38

[58] Field of Search .............. 536/27; 435/70.3, 6, 435/350

[56] References Cited

PUBLICATIONS

Chalfie, M., et al. The identification and suppression of inherited neurodegeneration in caenorhabditis elegans. Nature 1990; 345:410–416.
Savage, C., et al. Mec-7 is a B-tubilin gene required for the production of 15-protofilament microtubules in caenorhabditis elegans. Genes & Development 1989; 3:870–881.
Chalfie, M. et al. Genetic control of differentiation of the caenorhabditis elegans touch receptor neurons. Science 1989; 243:1027–1033.
Avery, L., et al. A cell that dies during wild-type C. elegans development can function as a neuron in a ced-3 mutant. Cell 1987; 51:1071–1078.
Kang, J. et al. The precursor of Alzheimer's disease amyloid A4 protein resembles a cell-surface receptor. Nature 1987; 325:733–736.
Ellis, H. M. et al. Genetic control of programmed cell death in the nematode C. elegans. Cell 1986; 44:817–829.
Hedgecock, E. M., et al. Mutations affecting programmed cell deaths in the nematode caenorhabditis elegans. Science 1983; 220:1277–1279.
Chalfie, M., et al. Developmental genetics of the mechanosensory neurons of caenorhabditis elegans. Developmental Biology 1981; 82:358–370.
Ellis et al. Nature 325:733–36 (1987).
Kang et al. Cell 44:817–29 (1986).
Nelson et al. Nucle. Acid. Res. 17(21):8647 (1989).
Ruvkun et al. Nucl. Acid Res. 18(4):809–(1990).
Cangiano et al. Nucleic. Acid Res. 18(17):5077–1990.
Seydour et al. Cell 61:939–51 (1990).
Herman R. Genetics. 116:377–388 (1987).
Brenner S. Genetics 77: 71–94 (1974).
Sulton et al. Genetics 77:95–104 (1974).
Coulson et al. P.N.A.S. 83:7821–25 (1986).
Rose et al. Mol. Gen Gen. 188:286–91 (1982).
Star et al Genome 32:365–72 (1989).

*Primary Examiner*—Robert A. Wax
*Assistant Examiner*—Miguel Escallon
*Attorney, Agent, or Firm*—John P. White

[57] ABSTRACT

This invention provides an isolated nucleic acid molecule encoding a wild-type animal protein associated with neuronal degeneration and an isolated nucleic acid molecule encoding a mutated animal protein associated with neuronal degeneration. Also provided are strains of the nematode *Caenorhabditis elegans* containing the nucleic acid molecules encoding a mutated *C. elegans* protein associated with neuronal degeneration. The invention also provides methods for detecting such nucleic acid molecules, for diagnosing degenerative disease, for causing a diseased human cell to degenerate, and for screening drugs to identify drugs which prevent or decrease neuronal degeneration.

7 Claims, 18 Drawing Sheets

FIGURE 2
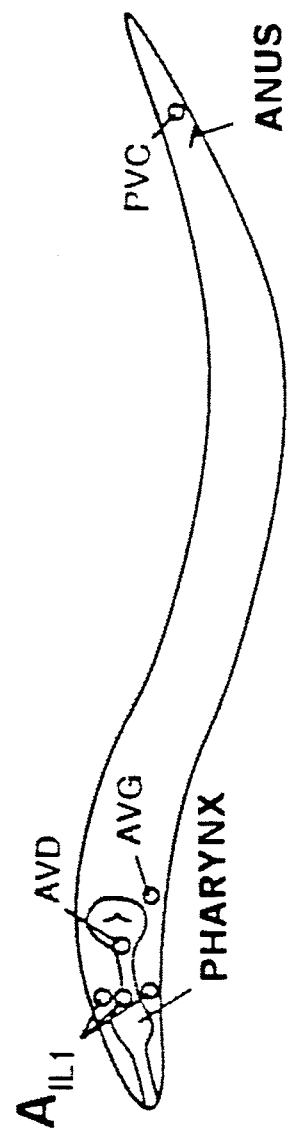
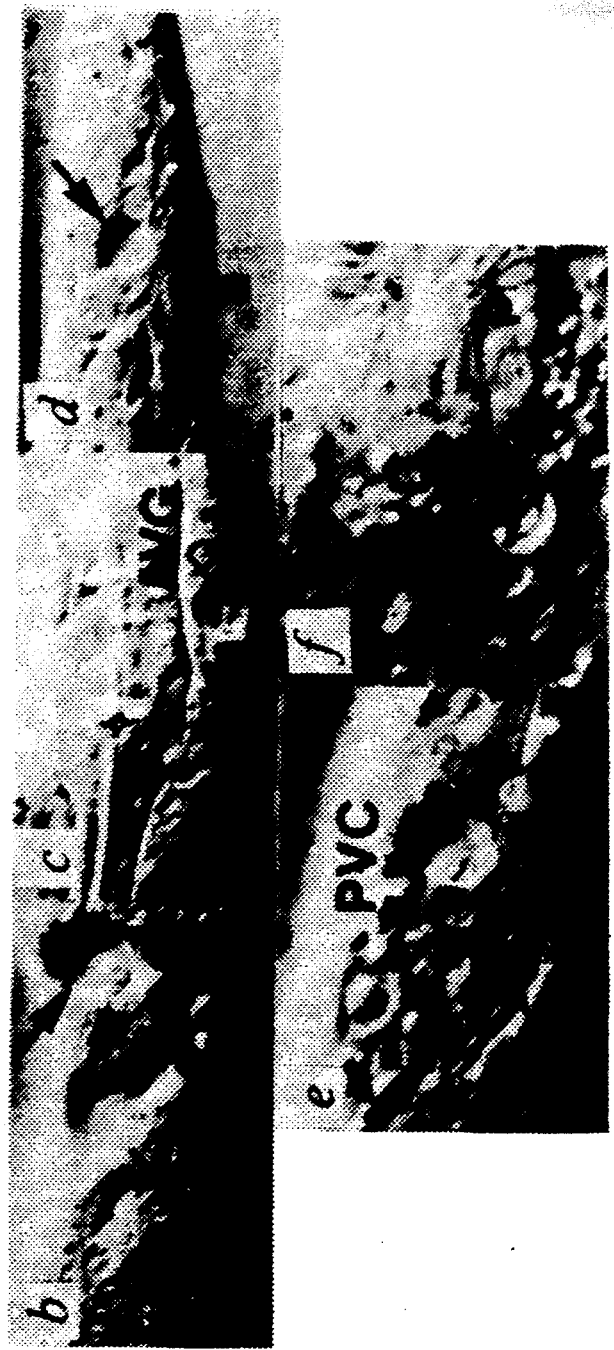

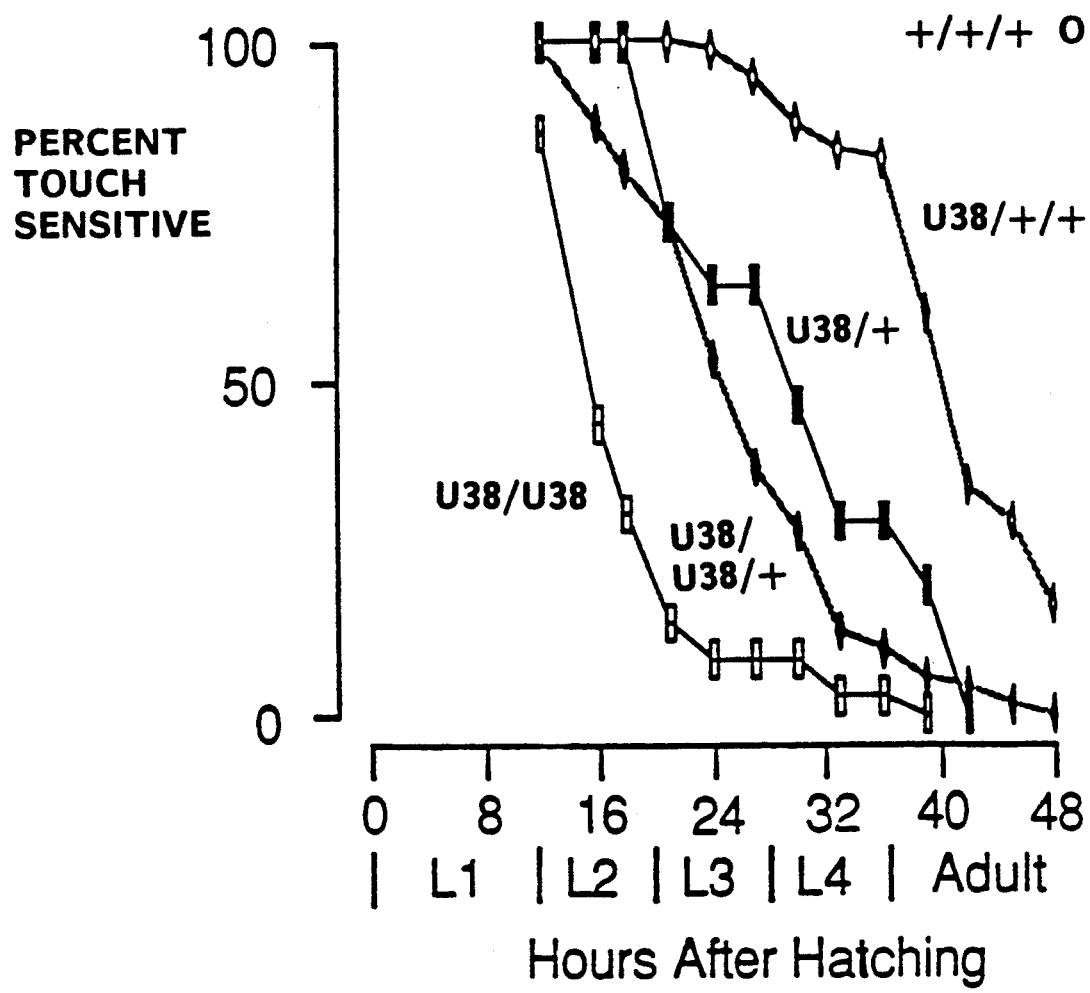

FIGURE 6
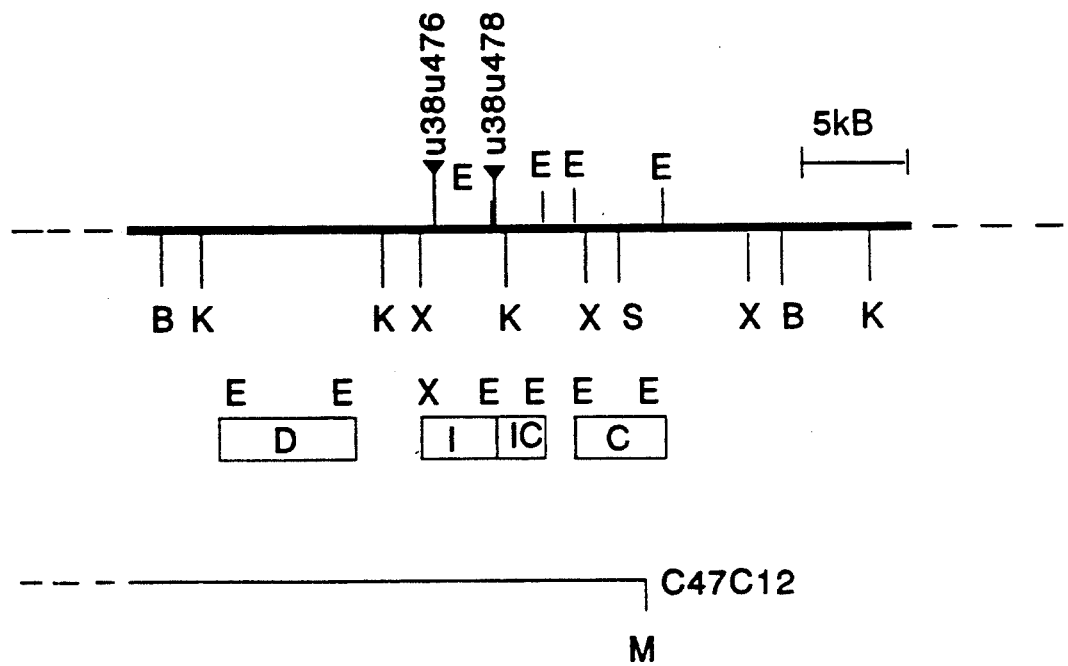
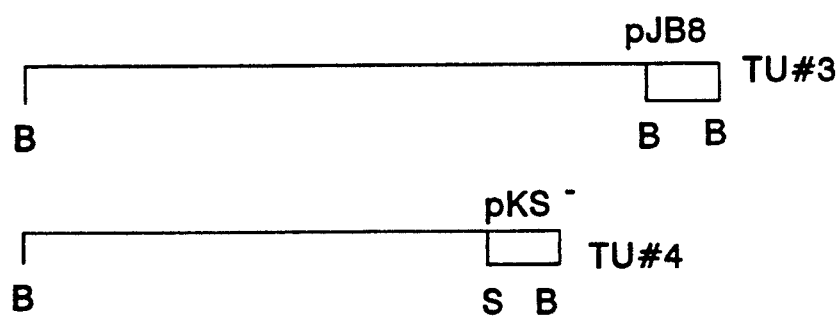

FIGURE 7A

| FIGURE 7 |
|---|
| FIGURE 7A |
| FIGURE 7B |
| FIGURE 7C |
| FIGURE 7D |

```
     1           10              20              30              40              50              60
GA  ATT CGT GTC CTT CTA AAC ACA TCA GAT TAT ATG TCA ACT TCT GAG TCA TCC GGA
    Ile Arg Val Leu Leu Asn Thr Ser Asp Tyr Met Ser Thr Ser Glu Ser Ser Gly
    1                           10                                              20

70              80              90             100             110             120
GTT CGA CTG GCC ATC CAT CCA ACT GAG TAC CCG GAC ACA TTC GGC TAT TCT
Val Arg Leu Ala Ile His Pro Thr Glu Tyr Pro Asp Thr Phe Gly Tyr Ser
21                          30                                              40

130             140             150             160             170             180
GCG CCA GTT GGT TTT GCA AGT AGT TTT GGA ATC AAA AAG GTG ATG CAA AGG TTG CCA
Ala Pro Val Gly Phe Ala Ser Ser Phe Gly Ile Lys Lys Val Met Gln Arg Leu Pro
41                          50                                              60

190             200             210             220             230             240
GCA CCA TAT GGA GAA TGT GTA GAA ACG AAG AAA GTT GTA GAC AGA AAT TAT ATT TAC GCG
Ala Pro Tyr Gly Glu Cys Val Glu Thr Lys Lys Val Val Asp Arg Asn Tyr Ile Tyr Ala
61                          70                                              80
```

FIGURE 7B

```
     250         260         270         280         290         300
GGG TAC GAT TAT CAT CCA GAA GGT TGT CAT AGA AGT TGC TTC CAA AAT GGA CTG ATT GAT
Gly Tyr Asp Tyr His Pro Glu Gly Cys His Arg Ser Cys Phe Gln Asn Gly Leu Ile Asp
 81                                     90                                  100

310         320         330         340         350         360
GAT TGT TCG TGT GGA GAT CCT CGT TTC CCA GTA CCA GAA GGT TAT AGA CAT TGC TCG GCA
Asp Cys Ser Cys Gly Asp Pro Arg Phe Pro Val Pro Glu Gly Tyr Arg His Cys Ser Ala
101                                     110                                 120

370         380         390         400         410         420
TTT AAT GCA ACA GCT CGT ACC TGT CTT GAG AAG AAC ATT GGC TCA GTT GGA GAT TTC CAT
Phe Asn Ala Thr Ala Arg Thr Cys Leu Glu Lys Asn Ile Gly Ser Val Gly Asp Phe His
121                                     130                                 140

430         440         450         460         470         480
CAT ATC ACT CAA AAA ATG GAC AAA TGC GTG TGT AAG CAA TCA TGT GAA ATT ATT CAT
His Ile Thr Gln Lys Met Asp Lys Cys Val Cys Lys Gln Ser Cys Glu Ile Ile His
141                                     150                                 151

490         500         510         520         530         540
GAA GTT ACC TTT TCA TGC TCC AAA TGG CCT TCG GGA GCT ACT GAC CTT GGA GAC TGT GAT
Glu Val Thr Phe Ser Cys Ser Lys Trp Pro Ser Gly Ala Thr Asp Leu Gly Asp Cys Asp
161                                     170                                 180
```

FIGURE 7C

```
         550             560             570             580             590             600
GGT ATG ACA GAA AGC GAG TGC GAA CAA TAC TAT CGG CTA AAT GCG GCA ATG ATC GAG GTA
Gly Met Thr Glu Ser Glu Cys Glu Gln Tyr Tyr Arg Leu Asn Ala Ala Met Ile Glu Val
181                             190                             200

610             620             630             640             650             660
TTC TAC GAA CAA CTG AAC TAC GAA CTG CTT CAA GAA TCA GAG GCA TAC GGT TTG GTT AAC
Phe Tyr Glu Gln Leu Asn Tyr Glu Leu Leu Gln Glu Ser Glu Ala Tyr Gly Leu Val Asn
201                             210                             220

670             680             690             700             710             720
TTG ATC GCC GAT TTT GGA GGA CAT TTA GGA CTT TGG CTA GGA TTC TCC GTA ATC ACC GTG
Leu Ile Ala Asp Phe Gly Gly His Leu Gly Leu Trp Leu Gly Phe Ser Val Ile Thr Val
221                             230                             240

730             740             750             760             770             780
ATG GAA GTT TGT GTT CTG CTT GTT GAT ATG ATT TCC CTT TTC TTT AAA AGT CGG CAC GAA
Met Glu Val Cys Val Leu Leu Val Asp Met Ile Ser Leu Phe Phe Lys Ser Arg His Glu
241                             250                             260

790             800             810             820             830             840
GAA AAA CTT CTG AGA CAG AGC ACA AAA AGG AAA GAT GTT CCA GAA GAT AAA CGG CAA ATT
Glu Lys Leu Leu Arg Gln Ser Thr Lys Arg Lys Asp Val Pro Glu Asp Lys Arg Gln Ile
261                             270                             280
```

FIGURE 7D

```
        850         860         870         880         890         900
ACA GTT GGA TCA GGG CGA AAG TCA GAC GCT TTC GTA TCA ATA TAA ATA CCA ACT CTC TTT
Thr Val Gly Ser Gly Arg Lys Ser Asp Ala Phe Val Ser Ile STOP
281                                             290

910         920         930         940         950         960
TGA ACA ACT ATT ATA TAA CGT TAA TTT TGA ACT GGG TTT CTC AAG ATG TAG TAT ACA ATG 970         980         990        1000        1010        1020
CTG TAA CAC GTT TCA CCT TTT TCC GAT CTC TAA TTG TAT ATA GTG AGC TTT

TTG ATT A
        90
```

FIGURE 9

| FIGURE 9A |
| FIGURE 9B |
| FIGURE 9C |
| FIGURE 9D |

FIGURE 9A

```
         10         20         30         40         50         60
GGAATGGGATGGAATGAAGAATATGAAGAATGACAATTATGAGAATTACGATGTGAAGC
         MetGluGlyMetGluAsnMetSerAsnTyrGluIleTyrAspValGluAl 70         80         90        100        110        120
AACTACTGGAATGAATGAATATGGAAGAATGTCAATCAGAGAGAACAAATTCGACGAGCCC
aThrThrGlyMetAsnMetMetGluGlyMetGluCysGlnSerGluArgThrAsnSerPr 130        140        150        160        170        180
GACGGGATTTGACGATCGGTGTATTGCGCTTTCGATAGATCAACTCATGATGCCGTGGCC
oThrGlyPheAspAspArgCysIleCysAlaPheAspArgSerThrHisAspAlaTrpPr 190        200        210        220        230        240
CTGTTTCTGAACGAACCTGGAAACCACCGAATGTGATACTTGCAATGAACATGCTTT
oCysPheLeuAsnGlyThrThrProGluThrTrpCysAspThrCysAsnGluHisAlaPh 250        260        270        280        290        300
CTGCACCAAAGATAACAAACTGCGAAGGCCATAGATCCCCATGTATTTGTCTCCATC
eCysThrLysAspAsnLysThrAlaLysGlyHisArgSerProCysIleCysAlaProSe 310        320        330        340        350        360
TAGATTCTGTGTAGCATACAACGAAAGACGCCACCAATTGAAATTTGGACATATCTCA
rArgPheCysValAlaTyrAsnGlyLysThrProProIleGluIleTrpThrTyrLeuGl 370        380        390        400        410        420
AGGAGGAACTCCAACTGAAGATCCAAACTTCCTTGAAGCTATGGGATTTCAGGGAATGAC
nGlyGlyThrProThrGluAspProAsnPheLeuAlaMetGlyPheGlnGlyMetTh 430        440        450        460        470        480
AGATGAAGTTGCAATTGTCACTAAAGCCAAGGAAAACATCATGTTTGCAATGGCTACCTT
rAspGluValAlaIleValThrLysAlaLysGluAsnIleMetPheAlaMetAlaThrLe
```

FIGURE 9B

```
        490       500       510       520       530       540
GTCAATGCAAGATAGGGAACGGCTAAGTACTACAAAAGGGAACTTGTCCACAAGTGCTC
uSerMetGlnAspArgGluArgLeuSerThrThrLysArgGluLeuValHisLysCysSe 550       560       570       580       590       600
GTTTAACGGAAAAGCCGTGTGATATCGAAGCAGATTTCTGACTCATATTGACCCTGCGTT
rPheAsnGlyLysAlaCysAspIleGluAlaAspPheLeuThrHisIleAspProAlaPh 610       620       630       640       650       660
TGGTTCGTGCTTTACCTTCAATCATAATCGAACAGTAAACTGACTAGTATTCGAGCAGG
eGlySerCysPheThrPheAsnHisAsnArgThrValAsnLeuThrSerIleArgAlaGl 670       680       690       700       710       720
TCCCATGTACGGATTACGTCGGTTTATGTAAACGCGTCTGACTATATGCCAACCAC
yProMetTyrGlyLeuArgMetLeuValTyrValAsnAlaSerAspTyrMetProThrTh 730       740       750       760       770       780
GGAAGCCACAGGCGTTCGTTGACTATTCATGACAAAGAAGATTTCCCATTTCCTGATAC
rGluAlaThrGlyValArgLeuThrIleHisAspLysGluAspPheProProAspTh 790       800       810       820       830       840
GTTCGGTTATTCTGCTCCAACTGGATATGTATCCTCATTTGGATTACGATTGCGAAAGAT
rPheGlyTyrSerAlaProThrGlyTyrValSerSerPheGlyLeuArgLeuArgLysMe 850       860       870       880       890       900
GTCACGTTTGCCAGCACCTTATGGAGATTGTGTGCCAGATGGCAAAACATCGGACTATAT
tSerArgLeuProAlaProTyrGlyAspCysValProAspGlyLysThrSerAspTyrIl
```

FIGURE 9C

```
       910          920         930         940         950         960
TTACAGCAATTATGAATATTCGGTAGAGGGCTGCTACCGTTCTTGCTTCCAACAACTCGT
eTyrSerAsnTyrGluTyrSerValGluGlyCysTyrArgSerCysPheGlnLeuVa 970         980         990        1000        1010        1020
GCTGAAAGAGTGCAGATGTGGAGATCCACGTTTCCAGTCCCTGAAAATGCACGGCATTG
lLeuLysGluCysArgCysGlyAspProArgPheProValProGluAsnAlaArgHisCy 1030        1040        1050        1060        1070        1080
CGATGCAGCAGACCCTATTGCAAGAAAATGTCTTGACGCCAGAATGAATGACTTGGGAGG
sAspAlaAlaAspProIleAlaArgLysCysLeuAspAlaArgMetAsnAspLeuGlyGl 1090        1100        1110        1120        1130        1140
CCTACACGGATCTTTCCGTTGCAGATGCCAACAACCATGCCCAGTCAATCTACTCCGT
yLeuHisGlySerPheArgCysArgCysGlnProCysArgGlnSerIleTyrSerVa 1150        1160        1170        1180        1190        1200
TACATACTCGCCGGCAAAGTGGCCCGTCGTTATCTTTGCAAATTCAACTAGGATCGTGTAA
lThrTyrSerProAlaLysTrpProSerLeuGlnIleGlnLeuGlySerCysAs 1210        1220        1230        1240        1250        1260
TGGTACAGCGGTAGAGTGTAATAAGCATTATAAAGAGAACGGAGCAATGGTGGAAGTGTT
nGlyThrAlaValGluCysAsnLysHisTyrLysGluAsnGlyAlaMetValGluValPh
```

FIGURE 9D

```
      1270       1280       1290       1300       1310       1320
CTACGAGCAGTTGAATTTGAAATGCTCACTGAATCAGAGGCTTATGGGTTTGTCAACTT
eTyrGluGlnLeuAsnPheGluMetLeuThrGluSerGluAlaTyrGlyPheValAsnLe
             *
      1330       1340       1350       1360       1370       1380
GCTAGCCGATTTTGGTGGACAACTCGGTCTTTGGTGTGCGGAATATCCTTCCTTACCTGTTG
uLeuAlaAspPheGlyGlyGlnLeuGlyLeuTrpCysGlyIleSerPheLeuThrCysCy 1390       1400       1410       1420       1430       1440
CGAATTTGTCTTCCTTTCTTGGAAACTGCCTACATGAGTGCCGAACATAACTACTCTCT
sGluPheLeuPheValPheLeuGluThrAlaTyrMetSerAlaGluHisAsnTyrSerLe 1450       1460       1470       1480       1490       1500
GTACAAAGAAGAAGGCTGAGAAGGCAAAGAAAATTGCGTCGGATCTTCTGAATTTG
uTyrLysLysLysLysAlaGluLysLysIleAlaSerGlySerPheEnd 1510       1520       1530       1540       1550       1560
TTTTTCTTGTTTAAAGTTACCAATGTTGTGTCTTAAATAAAATTTACATGA 1570       1580       1590       1600
GAATATAAAAAAAAAAAAAAAAAAAAAAAAAAAAAAAAA
```

* Site of dominant mutations.

FIGURE 11A mec-4-deg-1 homology

```
──────────────────────────── 494 aa   mec-4
        ──────────────────── 293 aa   deg-1
```

```
m4prot  LRMLVYVNASDYMPTTEATGVRLTIHDKEDFPFPDTFGYSAPTGYVSSFGLRLRKMSRLP
        : :::::::::::::.::::::         .::::::::::::::: :::  . .:::
degpro  IRVLLFVNTSDYMSTSESSGVRLAIHPPTEYPFPDTFGYSAPVGFASSFGIKKKVMQRLP m4prot  APYGDCVPDGKTSD--YIYSNYEYSVEGCYRSCFQQLVLKECRCGDPRFPVPENARHCDA
        ::::: .: . :    X:: .: :   :::::::::::          ::::::: ::::
degpro  APYGECVETKKVVDRNYIYAGYDYHPEGCHRSCFQNGLIDDCSCGDPRFPVPEGYRHCSA
```

FIGURE 11

| FIGURE 11A |
|---|
| FIGURE 11B |

FIGURE 11B

```
m4prot  ADPIARKCLDARMNDLGGLHGSF----RCRCQQPCRQSIYSVTYSPAKWPSLSLQIQLGS
        .::.::.  ........:        .:  .::v: . :.:.:. .:::: . .:::.
degpro  FNATARTCLEKNIGSVGDFHHITQKMDKCVCKQSCEEIIHEVTFSCSKWPSGA--TDLGD

*
m4prot  CNG-TAVECNKHYKENGAMVEVFYEQLNFEMLTESEAYGFVNLLI[A]DFGGQLGLWCGISFL
        :.: :. :.:  . : .:  ::::::::.:: :::::::: :::: ::::.:::::. :.
degpro  CDGMTESECEQYYRLNAAMIEVFYEQLNYELLQESEAYGLVTLIA DFGGHLGLWLGFSVI Charged m4prot  TCCEFVFLFLE--TAYMSAEHNYSLYKKKKAEK
        :  :: .:  . :. .::  .: ..::.    :
degpro  TVMEVCVLLVIMISLFFKSRHEEKLLRQSTKRK
```

* mec-4 dominant alleles change Ala at position 438 to Val or Thr

DNA SEQUENCES INVOLVED IN NEURONAL DEGENERATION, MULTICELLULAR ORGANISMS CONTAINING SAME AND USES THEREOF

This invention was made with support under Grant No. GM34775 from the National Institute of Health, U.S. Department of Health and Human Resources. Accordingly, the U.S. government has certain rights in the invention.

BACKGROUND OF THE INVENTION

Throughout this application various publications are references by Arabic numerals within parentheses. Full citations for these references may be found at the end of the specification immediately preceding the claims. The disclosures of these publications in their entireties are hereby incorporated by reference in this application in order to more fully describe the state of the art to which this invention pertains.

Neuronal cell death is a major feature of a variety of human neurological disorders, including the neurodegenerative diseases (such as Alzheimer's, Parkinson's, Huntington's and amyotrophic lateral sclerosis), stroke and trauma (67). Alzheimer's Disease afflicts about 4 million people in the United States, primarily the elderly. It is characterized by progressive memory loss, disorientation, depression and eventual loss of bodily functions. Amyotrophic lateral sclerosis, afflicts about 30,000 Americans. It begins after age 40 and results in progressive weakness and paralysis. Huntington's Disease, which afflicts an estimated 25,000 patients in the United States, usually begins between the ages of 30 and 50 and includes violent, involuntary movements. Cell death occurs not only as a disease process, but also as a normal aspect of development and of tissue homeostasis (68, 69, 70). Studies of both normal and abnormal cell deaths that occur in organisms as diverse as mammals, insects and nematodes have suggested that many of the distinct primary events that initiate the process of cell death act by triggering one of only a few general mechanisms that cause cells to die (71). If so, an understanding of cell death processes gained from any of these experimental systems might help reveal aspects of the cell death processes that occur in human diseases.

The mechanisms of cell death of one free-living nematode, *Caenorhabditis elegans* can be studied. In *C. elegans*, cell death can be observed in living animals at the level of resolution of single, identified cells (11). In addition, *C. elegans* is easily studied genetically, which not only allows the isolation of mutants with neurodegenerative genetic disorders that might serve as models for human disease, but more generally allows the identification of the genes and proteins that function in cell death. The mechanisms of cell death in wild-type and/or in mutant *C. elegans* may be similar to those involved in human disease. Furthermore, the genes and gene products involved in *C. elegans* cell death processes may be sufficiently conserved to allow the identification of corresponding molecules that cause human nerve cell deaths. Recent observations have revealed a striking degree of conservation of gene and protein structure among eukaryotic organisms. For example, many of the genes involved in nervous system development and function in *C. elegans* or in the fruit fly *Drosophila melanogaster* have proved to have easily recognized homologs in mammals. Programmed cell death is a prominent feature of *C. elegans* neural development. For example, the generation of the 816 nongonadal nuclei of the adult hermaphrodite is accompanied by the generation and death of an additional 131 cells (10, 11). About 80% (105/131) of these deaths involve cells that are neural in nature, and 23% (105/463) of all neural cells generated undergo programmed cell death (72).

During the course of *C. elegans* programmed cell death, a dying cell shrinks, becomes engulfed by a neighboring cell and eventually disappears (10, 11, 73). In the earliest stage of the programmed deaths of cells in the ventral nervous system, which are the cell deaths that have been studied in the most detail, the chromatin forms granular aggregates underlying the nuclear envelop, a cluster of electron-dense particles appears in the center of the nucleus, the nuclear envelop dilates, and both the nucleus and the cytoplasm become more electron dense. Next, the chromatin condenses further (so that very little euchromatin remains visible), the nucleus becomes pycnotic, mitochondria become electron-lucent, and parts of the dying cell split off into membrane-bound fragments. Later, the nuclear membrane becomes highly convoluted, nuclear membrane-bound structures (some containing chromatin-like material) are formed, mitochondria appear distorted (and frequently are found within vacuoles), the cytoplasm appears less granular than before, both internal and plasma membranes display increased whorling, and the cellular outline becomes irregular. Finally, as the dying cell is shrinking, the nuclear membrane breaks down completely, and chromatin-like fragments appear within the cytoplasm. Throughout this process, cytoplasmic extensions from neighboring cells encircle and engulf the dying cell. Genetic studies of *C. elegans* programmed cell death have defined an 11-gene pathway that functions in all programmed cell deaths (FIG. 8). These genes define three general processes: the death of a viable and potentially functional cell; the engulfment of the dying cell by neighboring cells; and the degradation of residual cellular debris. The one gene identified that functions in this third step is nuc-1 (nuc, nuclease-defective), which encodes or regulates a deoxyribonuclease (DNase) that degrades the DNA in dead cells (74). Seven genes (ced-1, ced-2, ced-5, ced-6, ced-7, ced-8, ced-10) (ced, cell death abnormal) function in the process of phagocytosis of dying cells by their neighbors (74). Mutations that eliminate the nuc-1 DNase activity or that block engulfment do not in general prevent the deaths of cells undergoing programmed cell death, so neither the nuclease nor the process of engulfment is causing these cells to die.

Three genes function in the killing of cells during programmed cell death: ced-, ced-4 and ced-9. Mutations that eliminate the activity of either ced-3 or ced-4 prevent the deaths of all 131 cells that normally die (19). In ced-3 or ced-4 animals, the "undead" cells not only survive, but they also can differentiate and express characteristics of other cells normally present in the animal; different surviving cells differentiate into different cell types. A surviving cell can be sufficiently normal that it is functional: one surviving cell in the animal's pharynx has been shown to acquire characteristics like those normally expressed by its sister, the M4 motor neuron; if the M4 neuron is killed (using a laser microbeam) in a ced-3 mutant animal, the surviving sister of the M4 neuron is capable of replacing it functionally (20). These observations indicate that the genes ced-3 and ced-4 normally act to convert live, potentially functional cells into non-functional cell corpses. In brief, ced-3 and ced-4 cause cells to die.

These "killer genes", ced-3 and ced-4, may act within the dying cells themselves or within other cells that function to cause dying cells to die (75). To determine this, the technique of genetic mosaic analysis was used. Specifically, animals with cells of different genotypes—for example, with some cells wild-type for the ced-3 gene and other cells mutant for the ced-3 gene—were constructed, and it was determined whether the ced genotype of a cell that should die determined whether or not that cell would die in a mosaic animal. The results of these studies revealed that both ced-3 and ced-4 act autonomously, i.e. both of these genes act within dying cells to cause their deaths. These observations indicate that programmed cell death in C. elegans is an active process on the part of dying cells, requiring the functions of gene products that act within the cells that die.

That the two genes known to be required for cells to die during programmed cell death both act within dying cells suggests that the cell death process itself might be cell autonomous. In other words, programmed cell death in C. elegans might be a suicide rather than a murder. A number of other observations are consistent with this hypothesis. For example, many dying cells are smaller than their sisters at the times of their births, suggesting that their fates have already been specified (10, 11). In addition, most dying cells die within an hour of their births, before any overt signs of differentiation (10, 11), which indicates that these cells are unlikely to be dying as a consequence of a failure to compete for targets. Nonetheless, it remains possible that some programmed cell deaths are initiated by cell interactions that activate ced-3 and ced-4 within the cells that die.

The third gene that acts in the killing step of programmed cell death is ced-9. The original ced-9 mutant strain is phenotypically similar to the ced-3 and ced-4 mutants described above: all programmed cell deaths are blocked. However, the ced-9 mutation in this strain is opposite in nature to the ced-3 and ced-4 mutations that have been studied. Specifically, cell death is prevented by mutations that cause a loss of ced-3 and ced-4 gene function or a gain of ced-9 gene function. These observations indicate that whereas ced-3 and ced-4 normally act to cause cells to die, ced-9 might normally act to prevent cells from dying. Further genetic analyses of ced-9 have strengthened the hypothesis that this gene encodes a product that protects cells from programmed cell death.

The studies described above indicate that programmed cell death can be regarded as a cell fate, analogous to any differentiated fate, such as becoming a muscle cell or a dopaminergic neuron. Specifically, all cells that undergo programmed cell death display the same sequence of morphological changes and require the same set of genes, and hence proteins. Thus, the same physiological processes seem to act in all programmed cell deaths in C. elegans. As in the cases of other cell fates, programmed cell death seems likely to involve functions responsible both for determination—the specification of which cells will and which cells will not die—and for differentiation—the expression of the cell death fate itself. The 11 genes discussed above are involved in this latter step, as they carry out programmed cell death. Genes that act in the determinative aspect of programmed cell death would be recognized by their altering patterns of cell death without affecting the machinery necessary for the cell death process. Such genes would include those that could mutate to cause specific cells that normally survive instead to undergo programeed cell death. This phenotype would constitute a degenerative genetic disorder of C. elegans.

One neurodegenerative genetic disorder of this class has been identified in C. elegans. In egl-1 mutants (egl, egg-laying abnormal), the serotonergic HSN motor neurons, which normally innervate the egg-laying musculature and drive egg laying, die (19). No other cells have been found to be abnormal in egl-1 animals. The deaths of the HSNs in egl-1 animals appear morphologically identical to programmed cell deaths, require ced-3 and ced-4 gene function and are blocked by the gain-of-function mutation in ced-9. Thus, mutations in the egl-1 gene cause the highly specific neurodegeneration of the HSN neurons by ectopically activating the program for programmed cell death. It has been proposed (19) that the basis of this phenotype is a sexual transformation in the fate of the hermaphrodite-specific HSN neurons, the homologs of which undergo programmed cell death in males (10). The neurodegenerative phenotype of all egl-1 mutants is dominant.

This invention describes mutations in two other genes, mec-4 (mec, mechanosensory abnormal) (7, 8) and deg-1 (degeneration), which cause neurodegenerative genetic disorders of C. elegans. Unlike egl-1 mutants, in which the genes involved in programmed cell death are ectopically activated, mec-4 and deg-1 mutations cause cells to die independently of the ced genes discussed above. In mec-4 mutants, a specific set of six touch receptor neurons die. In deg-1 mutants, another small set of neurons, including both sensory and interneurons, die. Unlike the cells that die during programmed cell death, the cells that die in these degenerative deaths swell and lyse. The remains of the nucleus and cytoplasmic debris can be seen within a large vacuole many cell diameters in size.

SUMMARY OF THE INVENTION

This invention provides an isolated nucleic acid molecule encoding a wild-type animal protein, the mutated version of which is associated with neuronal degeneration. The invention further provides an isolated nucleic acid molecule encoding a mutated animal protein associated with neuronal degeneration.

In the nematode Caenorhabditis elegans, the wild-type animal protein may be encoded by the deg-1 gene. Furthermore, the mutated animal protein may be encoded by a mutant of the deg-1 gene, the deg-1 gene having the cDNA sequence shown in FIG. 7. Examples of mutants of the deg-1 gene are designated u38 or uIn1.

The wild-type animal protein in Caenorhabditis elegans may be encoded by the mec-4 gene. The mutated animal protein may be encoded by a mutant of the mec-4 gene, the mec-4 gene having the cDNA sequence shown in FIG. 9. Examples of mutants of the mec-4 gene are designated e1611, u214, or u231.

This invention further provides a Caenorhabditis elegans strain designated TU38 and deposited with the ATCC under Accession No. 40818; a Caenorhabditis elegans strain designated TU1191 and deposited with the ATCC under Accession No. 40817; a Caenorhabditis elegans strain designated CB1611 and deposited with the ATCC under Accession No. 40820; a Caenorhabditis elegans strain designated TU214 and deposited with the ATCC under Accession No. 40819; and a Caenorhabditis elegans strain designated TU231 and deposited with the ATCC under Accession No. 40821. Strains designated TU38, TU1191, CB1611, TU214 and TU231, received by the American Type Culture Collection (ATCC), 12301 Parklawn Drive, Rockville, Md. 20852.

The invention further provides a method for detecting a nucleic acid molecule encoding a wild-type protein associated with a degenerative disorder in a human subject which comprises obtaining a sample of DNA or mRNA from the subject, contacting the DNA or mRNA with a nucleic acid molecule encoding a wild-type human protein associated with neuronal degeneration, such nucleic acid molecule being labeled with a detectable moiety, under suitable conditions permitting hybridization of the DNA or mRNA and the nucleic acid molecule, and detecting the hybridized nucleic acid molecules, thereby detecting the nucleic acid molecule encoding the wild-type protein associated with the degenerative disorder.

Further provided is a method for detecting a mutation associated with a degenerative disorder in a human subject which comprises obtaining a sample of DNA or mRNA from the subject, contacting the DNA or mRNA with the nucleic acid molecule encoding a mutated human protein associated with neuronal degeneration, such nucleic acid molecule being labeled with a detectable moiety, under suitable conditions permitting hybridization of the DNA or mRNA and the nucleic acid molecule, and detecting the hybridized nucleic acid molecules, thereby detecting the mutation associated with the degenerative disorder.

Further provided is a method of diagnosing degenerative disease in a human subject which comprises detecting the presence of a mutation associated with a degenerative disorder using the methods disclosed above for detecting a mutation associated with a degenerative disorder.

The subject invention further provides a method of treating a degenerative disease in a human subject which comprises introducing into the human subject an amount of a nucleic acid molecule encoding a wild-type human protein associated with neuronal degeneration effective to suppress neuronal degeneration caused by mutants of the nucleic acid molecule, thereby decreasing neuronal degeneration in the human subject and treating the degenerative disease.

The subject invention also provides a method of causing a diseased human cell to degenerate which comprises introducing a nucleic acid molecule encoding a mutated human protein associated with neuronal degeneration into the diseased human cell so as to cause its degeneration, thereby causing the diseased human cell to degenerate.

The strains of Caenorhabditis elegans provided by the subject invention can also be used in a method of screening drugs to identify drugs which prevent or decrease neuronal degeneration which comprises contacting a Caenorhabditis elegans strain with a plurality of drugs, determining those drugs which prevent or decrease neuronal degeneration of the strain, and thereby identifying drugs which prevent or decrease neuronal degeneration.

The invention further provides a protein encoded by any one of the nucleic acid molecules disclosed herein.

Figure 1:
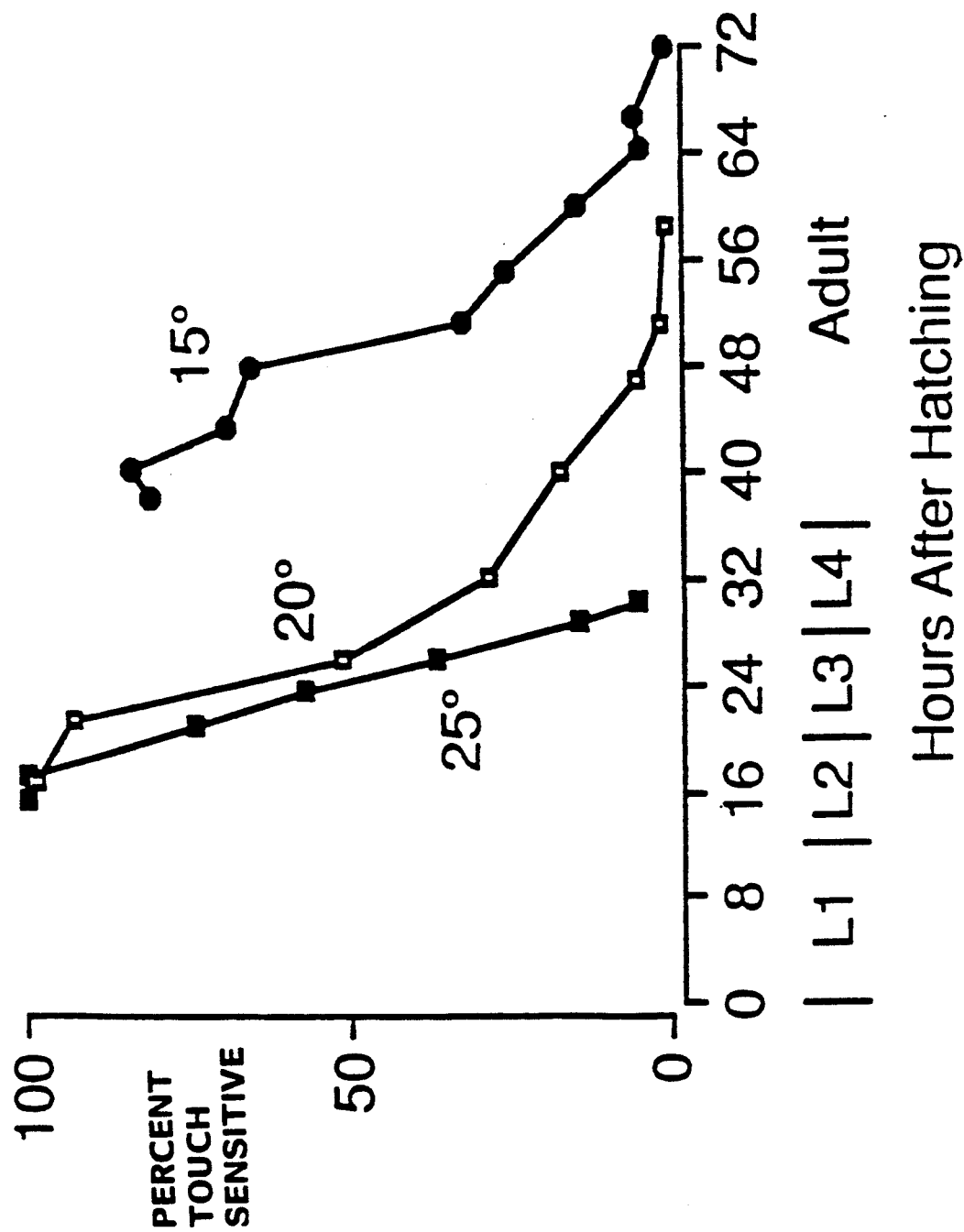
FIG. 1. Onset of the deg-1 touch-insensitivity (Tab) phenotype at various temperatures. The abscissa records time in 25 hour equivalents (C. elegans grows at approximately twice the 15° C. rate at 25° C.).

Methods: Strains were maintained on Escherichia coli strain OP50-1 as described previously (14, 57). Animals from strains grown at the indicated temperatures for at least two generations were synchronized at hatching by washing hatched animals and bacteria from the plates with M9 buffer (14) and collecting the larvae that hatched from the remaining eggs in the next 1-2 hours. At the indicated times animals were tested for touch sensitivity at the tail by touching with a thin hair (8). At least 100 animals were examined at each temperature.

The deg-1(u38) mutation maps within 0.014 map units of the mec-7 gene on the X chromosome by the following criteria: no wild-type progeny were found among 3533 total progeny from +[+deg-1(u38)]/lon-2(e678) [mec-7 (e1506)+] heterozygotes nor among 5334 and 5960 heterozygote progeny from, respectively, +[+deg-1(u38)]dpy-6(e14)/dpy-7(e88) [mec-7(e1506)+]+ and dpy-7[+deg-1(u38)]+/+[mec-7(e1506)+]dpy-6(e14) heterozygotes (11, 14). deg-1 loss-of-function mutations complement the recessive mec-7 allele e1506 for touch insensitivity, an indication that the two loci are different genes.

FIG. 2. Defects in deg-1 mutants. (a) Schematic diagram of the left side of newly-hatched C. elegans larva indicating the positions of some of the cells affected by the deg-1(u38) mutation. All of these neurons, except AVG, have homologues on the other side of the animal. These cells die at different times: the ILI sensory neurons and the AVG interneuron die at hatching, the PVC cells in the third larval stage (L3), and the AVD interneurons near the end of the last (L4) larval stage. Other degenerations are sometimes seen. Because the degenerations can be quite large, distorting the surrounding pattern of nuclei, it is difficult to identify unambiguously the affected cells. The pattern in u38 males does not differ substantially from that of hermaphrodites. (b) Differential interference contrast micrographs of deg-1 degenerative deaths (ILI and large arrow) and programmed cell deaths (small arrows) posterior to the first bulb of the pharynx (p) in a newly-hatched ced-1; deg-1 double mutant. (The ced-1 mutation e1735 delays the engulfment of cells dying by programmed cell death.) The two types of deaths are morphologically distinct. The cells here and in subsequent photomicrographs have been tentatively identified by criteria given below. Not all of the ILI cells die: one to three ILI cells (wild-type have six) were seen in six deg-1 adults examined by serial section electron microscopy (58, 59). Magnification ×800. (c) Putative AVG death in a newly-hatched larva. 24% (12/49) newly-hatched animals had this death. (d) Empty vacuole in the tail of a newly-hatched larva. Anus. (e) PVC death in 24 hour larva. (f) Putative AVD death at the time of the last larval molt (36 hours). Criteria for identifying cells: The dying cells were identified by their positions (59) and the following data. IL1: Cells with the characteristic rootlet (59) of the IL1 cells were missing in serial sections of the tip of the nose of adult animals. AVG: A single degeneration is seen in the retrovesicular ganglion just posterior to the rear bulb of the pharynx in many newly hatched animals. AVG is the only unpaired neuron in this region (60). AVD: This pair of interneurons helps mediate anterior touch sensitivity (9), but since the anterior touch circuit also utilizes other interneurons, loss of the AVD cells in the deg-1 mutants does not produce a Tab phenotype. However, laser ablation of the AVA interneurons in deg-1 animals results in animals that are virtually incapable of backward movement as young adults but not as larvae, a result seen in wild-type animals when both the AVA and AVD cells are ablated (9). PVC: See text.

Figure 3:
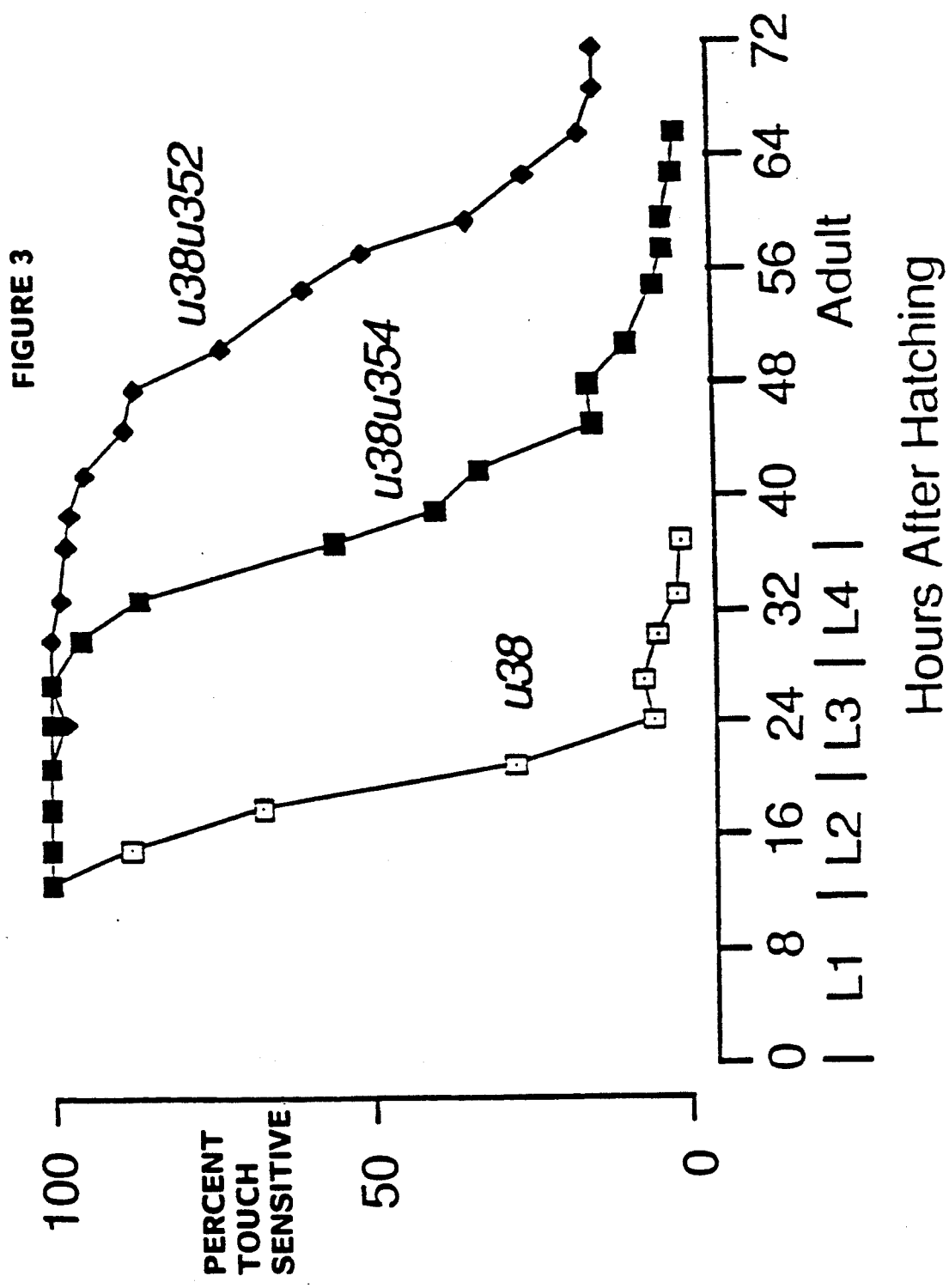

FIG. 3. Onset of the Tab phenotype in deg-1(u38) and two partially reverted strains [deg-1(u38u354) and deg-1(u38u352)]. Animals were grown from synchronized populations at 25° C. (FIG. 1). At least 100 animals of each strain were examined. The Tab phenotype, as in u38 mutants, is temperature dependent in u38u352 and u38u354 animals (data not shown). Not all deg-1-dependent deaths seem to be affected the same way by these suppressor mutations. The number of degenerations in newly hatched animals is reduced in u38u354 animals but not in u38u352 animals 2.9±0.3 deaths; n=20 for each; u38 animals have 2.2±0.2 deaths). Both suppressor-containing strains produce animals with the presumptive AVD deaths (FIG. 2) at 36 hours (5/11, 3/11 and 2/10 for u38, u38u352, and u38u354, respectively).

FIG. 4. Onset of the Tab phenotype in animals with different doses of the wild-type (+) and mutant (u38) alleles of deg-1. Progeny of hermaphrodites with the genotype stDp2/+; deg-1(u38)+dpy-6(e14)/unc-18(e81)+dpy-6(e14) were synchronized at hatching (FIG. 1 legend). At the indicated times after hatching animals that were Tab were plated individually so that their progeny could be examined so as to determine their genotypes. All animals that have three copies of the region [u38/u38/+(filled diamonds), u38/+/+ (open diamonds), and +/+/+ (open circle)] contain stDp2, a duplication of the dpy-6 deg-1 region of the X chromosome that has been translocated to chromosome II and is lethal when homozygous. All these animals are wild-type in length. At least 50 animals of each of these genotypes were examined. Animals with two copies of the region (u38/u38 (open bars) and u38/+ (filled bars) are homozygous for the dpy-6 mutation and are shorter in length (Dpy). Thirty-seven u38/u38 and eleven u38/+ animals were examined. The Dpy phenotype does not seem to affect the onset of the degeneration (compare FIG. 1). (The dpy and unc mutations are described in Reference 16.) Wild-type animals (+/+; not shown), like the +/+/+ animals, are touch sensitive at all times.

Figure 5A:
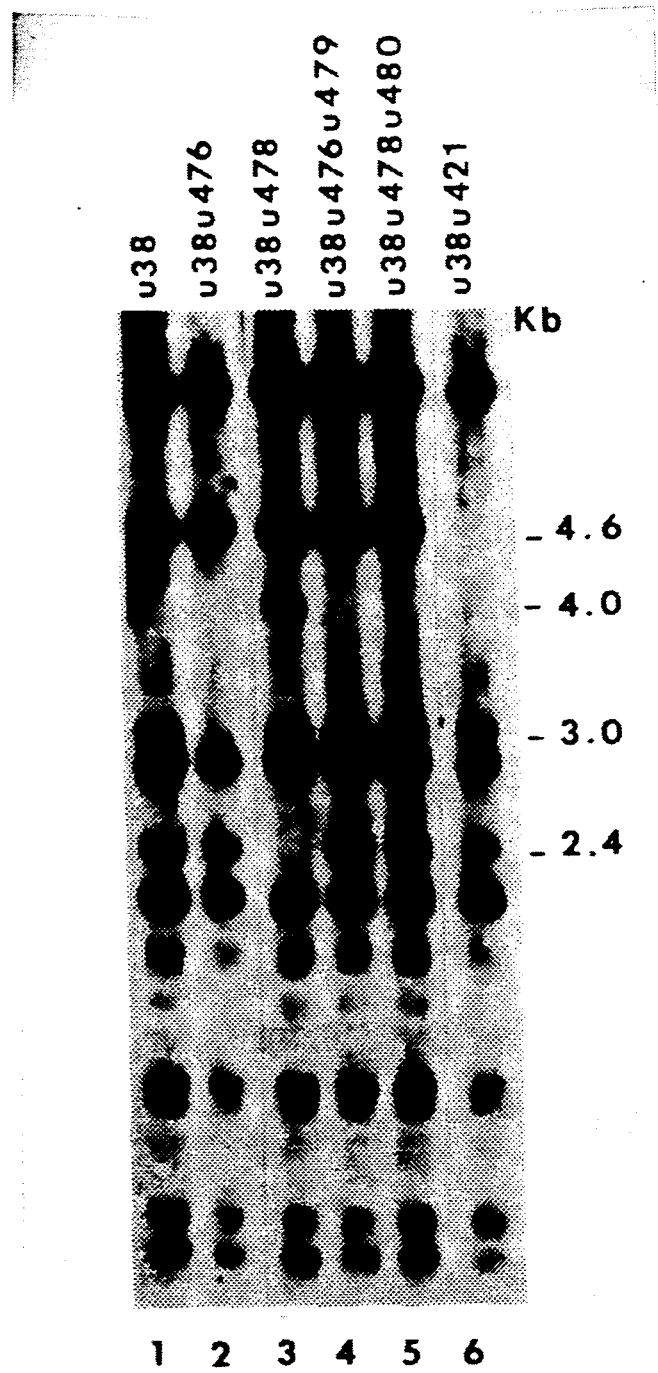

FIG. 5. Southern blot analysis of deg-1 DNAs.

a. Genomic DNA digested with EcoRI and XbaI and probed with cosmid C47C12. Lane 1, deg-1(u38); Lane 2, a mut-2-derived revertant of deg-1(u38) containing a Tc1 insertion in the 3.0 kb EcoRI-XbaI fragment (fragment I in FIG. 6; the resulting fragment with the insertion comigrates with a second fragment and increases the intensity of the band at 4.6 kb); Lane 3, a second revertant with an insert in the 2.4 EcoRI fragment (fragment IC in FIG. 6); Lanes 4 and 5, excision strains from deg-1(u38u476) and deg-1(u38u478), respectively, which express the Deg and Tab phenotypes; Lane 6, an EMS-derived revertant missing the 4.5 kb EcoRI fragment (fragment D in FIG. 6). No differences in the hybridization pattern were detected between deg-1(u38) and wild-type DNA probed with cosmid C47C12 or RO2A8 (see FIG. 6). A third mut-2-derived revertant, u38 u477, also had the same pattern of hybridization as the wildtype.

b. Genomic DNA digested with EcoRI and XbaI and probed with fragment IC. The IC fragment hybridizes to the deg-1 cDNA and contains the insertion site of the Tc1 transposon in revertant strain u38u478. Lane 1, deg-1(u38); Lane 2, deg-1(u38u478). Five cross-hybridizing bands, which are also seen in the wild-type in other blots, are indicated by arrowheads.

Methods: C. elegans genomic DNA was prepared essentially as described (61). General molecular methods were as described (62) with final washes of blots in 0.1X SSC at 65° C. Initially deg-1 DNA was cloned from the u38u476 strain. Southern blots of DNA from this strain, when probed with DNA from the transposon Tc1 (61), revealed a single, novel Tc1-containing EcoRI/XbaI fragment I5 that cosegregated with the non-Tab phenotype in recombinants with u38. This fragment was isolated from a plasmid library constructed of size-fractionated EcoRI/XbaI fragments from u38u476 DNA in plasmid pUC18. The resulting plasmid was digested with EcoRV to remove the Tc1 element and religated to produce plasmid TU#8.

FIG. 6. DNAs of the deg-1 region. The top line represents a partial restriction map of genomic DNA. Triangles denote the approximate positions of transposon insertions in the indicated revertants (all insertions are 1.6 kb, the size of the transposon Tc1, but the presence of this transposon has been confirmed only in strain u38u476). The boxes under the restriction map indicate fragments that harbor DNA rearrangements in u38 revertants or that hybridize to deg-1 cDNAs; D is deleted in u38u421; I contains the Tc1 insertion in u38u476; IC contains the transposon insertion in u38u478 and hybridizes to the deg-1 cDNAs (the transposon resides in a 187 bp EcoRI/NdeI fragment at the 5' end of IC; the sequence of this fragment is identical with the deg-1 cDNAs, except for a 50 bp intron 160 bp from the EcoRI site); and C is a fragment that also hybridizes to the cDNAs. C47C12 and RO2A8 are cosmids containing wild-type DNA (24). TU#3 is a cosmid clone of the BamHI fragment from deg-1(u38); when transformed into wild-type animals, TU#3 produces the Deg and Tab phenotypes. TU#4 is a derivative of TU#3 that lacks the 3' SmaI/BamHI fragment and does not generate the Deg or Tab phenotypes on transformation into wild-type. B=BamHI, E=EcoRI, K=KpnI, S=SmaI, X=XbaI, M=MboI. Not all EcoRI, XbaI, and MboI sites are indicated.

Methods: Genomic subclones of wild-type DNA from C47C12 were made by ligation into pUC18. The TU#3 cosmid was obtained by isolating large fragments from BamHI-digested deg-1(u38) DNA from a sucrose gradient (64) and ligating them to the BamHI-HindIII and SalI-BamHI fragments of the cosmid vector pJB8 (63). This library was screened with all four genomic fragments (D, I, IC, and C) individually as probes. Animals were transformed with TU#3 DNA by co-injection of the DNA into wild-type oocytes (64) with either pPD10.41 or pGB3.5, plasmids that contain an antisense construct of the C. elegans unc-22 gene that produces a twitching phenotype. About half of the twicher transformants also segregated animals that were Tab and Deg. uIn1 resulted from co-injection of TU#3 and pGB3.5 and showed linkage with unc-18(e81) on the X chromosome. Transformations with TU#4 were done similarly; southern blotting confirmed that TU#4 was present in the transformed animals.

FIG. 7. DNA and predicted protein sequence of a deg-1 cDNA. The sequence of the larger cDNA is shown. The smaller cDNA lacks the DNA encoding residues 176 to 199 (bracketed). Potential glycosylation sites (26) are underlined, cysteine residues are asterisked, and the hydrophobic region is double underlined.

Methods: The cDNAs were subcloned from λgt10 into the EcoRI site of pKS⁻ and pKS⁺ (Stratagene). Single stranded DNA was rescued from a set of nested deletions (65) using helper phage R408 (Stratagene) and sequenced by the dideoxy method (66) using either Klenow (New England Biolabs) or Sequenase (U.S. Biochemicals). Both strands were sequenced. Sequence comparison to Genbank, PIR and Claverie DNA and protein databases was performed using the DFASTN and DFASTP.

Figure 8:
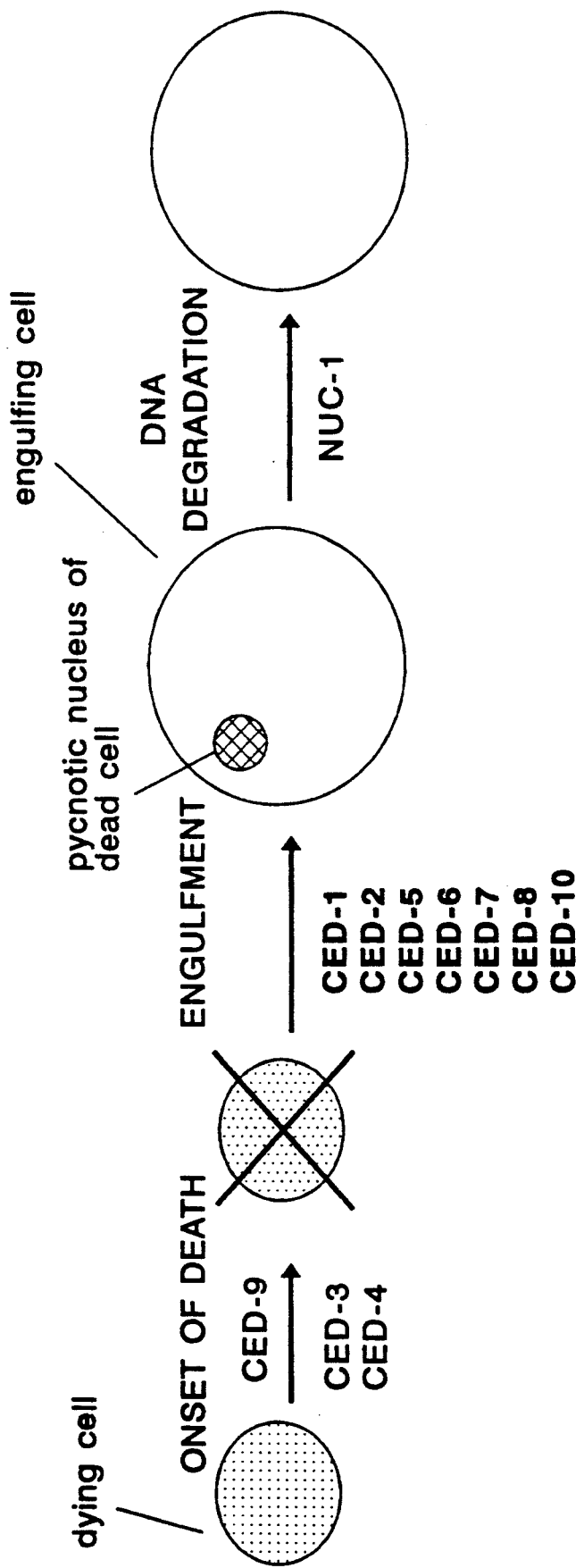

FIG. 8. Genetic pathway for programmed cell death in *C. elegans*. Two genes, ced-3 and ced-4, act to cause cells to die; mutations that block the activity of either ced-3 or ced-4 prevent cell death. The gene ced-9 appears to antagonize the action of ced-3 and ced-4; mutations that cause a gain of ced-9 function prevent programmed cell death. The activities of the genes ced-1, ced-2, ced-5, ced-6, ced-7, ced-8 and ced-10 are necessary for the phagocytosis of dying cells by their neighbors. If these genes fail to function, phagocytosis is blocked, but cell death still occurs. The gene nuc-1 acts to degrade the DNA of dying cells.

FIG. 9. DNA and predicted protein sequence of a mec-4 cDNA.

Figure 10:
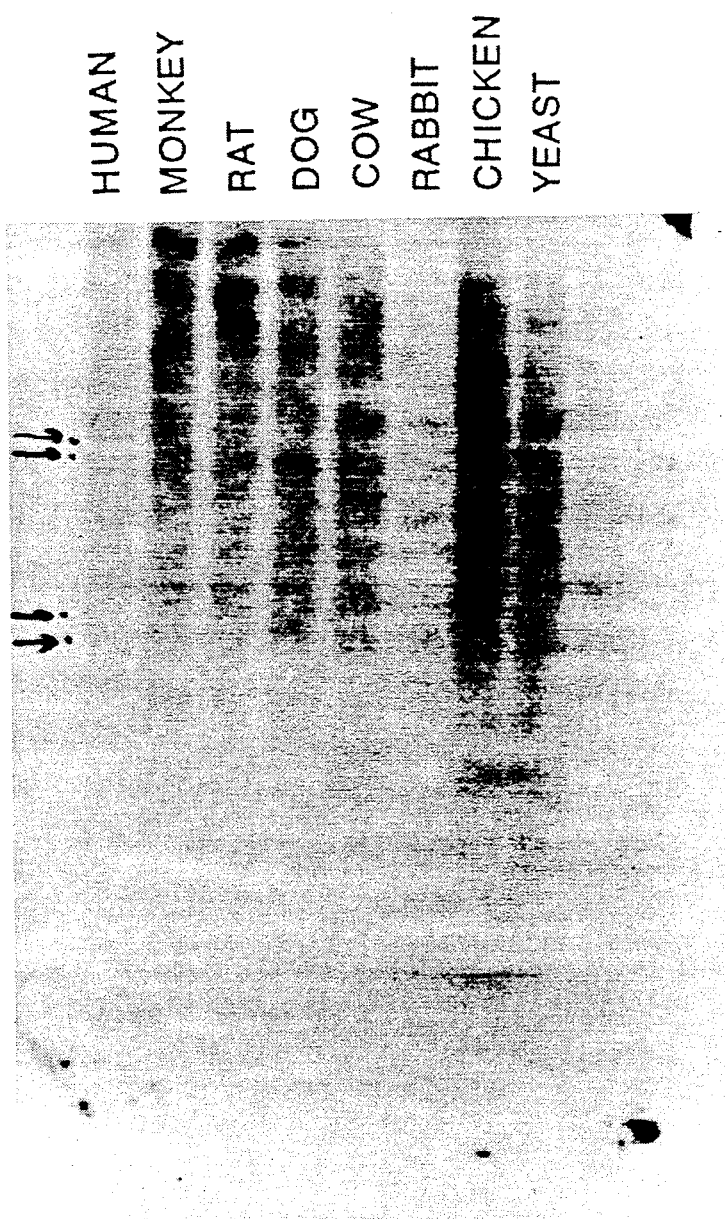

FIG. 10 Autoradiogram of mec-4 homology to various species. Southern blot where DNA from different species (i.e., human, monkey, rat, mouse, dog, cow, rabbit, chicken, and yeast) are probed with the mec-4 gene. Both the mouse and human lanes shown cross-hybridization with mec-4 indicating they may contain genes which are members of a gene family.

FIG. 11 mec-4-deg-1 homology. This figure shows the mec-4-deg-1 gene homology. The mec-4 dominant alleles change Ala at position 438 to Val or Thr as indicated.

DETAILED DESCRIPTION OF THE INVENTION

The *Caenorhabditis elegans* strains designated TU38, TU1191, CB1611, TU214, and TU231 were deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 40818, 40817, 40820, 40819, and 40821, respectively.

DEFINITIONS

In order to provide a clear and consistent understanding of the specification and claims, including the scope to be given such terms, the following definitions are provided.

Nematode: The term "nematode" is intended to refer generally to the class Nematoda or Nematoidea and comprises those animals of a slender cylindrical or thread-like form commonly called worms.

Mutant: The term "mutant," as in "nematode mutant" or "mutant nematode," is intended to refer generally to a nematode which contains a stably altered genotype. The altered genotype results from a mutation not generally found in the genome of the wild-type nematode.

Library: A "library" of nematodes is a collection of different nematodes and may include both wild-type and mutant nematodes.

Drug: The term "drug" is intended to refer to a chemical entity, whether in the solid, liquid, or gaseous phase which is capable of providing a desired therapeutic effect when administered to a subject. The term "drug" should be read to include synthetic compounds, natural products and macromolecular entities such as polypeptides, polynucleotides, or lipids and also small entities such as neurotransmitters, ligands, hormones or elemental compounds. The term "drug" is meant to refer to that compound whether it is in a crude mixture or purified and isolated.

Cell Death: By the term "cell death" is meant the process through which cells die. As referred to for the purposes of this invention, cell death is meant to exclude those processes wherein cells die as an immediate result of acute physical injury. By "late-occurring" cell death is meant cell death which occurs after the cell has become functional. For example, by late-occurring neuronal cell death is meant cell death which occurs after the neurons form synapses and become functional nerve cells.

Cloning Vehicle: By "cloning vehicle" is meant a plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, for example, are tetracycline resistance or ampicillin resistance. The word "vector" is sometimes used for "cloning vehicle."

Expression Vehicle: By "expression vehicle" is meant a vehicle or vector similar to a cloning vehicle but which is capable of expressing a gene which has been cloned into it, after transformation into a host The cloned gene is usually placed under the control of (i.e., operably linked to) certain control sequences such as promoter sequences. Expression control sequences will vary depending on whether the vector is designed to express the operably linked gene in a procaryotic or eucaryotic host and may additionally contain transcriptional elements such as enhancer elements, termination sequences, tissue-specificity elements, and/or translational initiation and termination sites.

Functional Derivative: A "functional derivative" of the proteins of the invention is a protein which possesses a biological activity (either functional or structural) that is substantially similar to a biological activity of such proteins. A functional derivative may or may not contain post-translational modifications such as covalently linked carbohydrate, depending on the necessity of such modifications for the performance of a specific function. The term "functional derivative" is intended to include the "fragents," "variants," "analogues," or "chemical derivatives" of a molecule.

Fragment: A "fragment" of a protein of the invention is meant to refer to any portion of the protein of the invention which contains less than the complete amino acid sequence of the protein.

Variant: A "variant" of a protein of the invention is meant to refer to a protein substantially similar in structure and biological activity to either the entire protein of the invention or to a fragment thereof. Thus, provided that two proteins possess a similar activity, they are considered variants as that term is used herein even if the composition or secondary, tertiary, or quaternary structure of one of the molecules is not identical to that found in the other, or if the sequence of amino acid residues is not identical.

Analog: An "analog" of the proteins of the invention is meant to refer to a protein substantially similar in function to either the native protein of the invention or to a fragment thereof. As used herein, a protein is said to be a "chemical derivative" of another protein when it contains additional chemical moieties not normally a part of the protein. Such moieties may improve the protein's solubility, absorption, biological half life, etc. The moieties may alternatively decrease the toxicity of the protein, eliminate or attenuate any undesirable side effect of the protein, etc. Moieties capable of mediating such effects are disclosed in *Remington's Pharmaceutical Sciences* (1980). Procedures for coupling such moieties to a protein are well-known in the art.

The subject invention identifies defective genes in roundworms that cause mature, functioning nerve cells to die. Such late-occurring nerve cell death is seen in several human disorders such as Huntington's, Lou Gehrig's (amyotrophic lateral sclerosis) and Alzheimer's diseases.

The subject invention provides scientists an animal model with which to study the causes of neurodegenerative disease. The findings will lead to ways to prevent and treat the human disorders, which afflict millions of people and have no known cures.

The invention discloses a gene called deg-1 (degeneration). A rare mutation in this gene causes a small set of cells in the nervous system of the microscopic roundworm *Caenorhabditis elegans* to die. Similar deaths, but of different nerve cells, are caused by rare mutations in a second gene called mec-4 (mechanosensory abnormal). As with many inherited human neurodegenerative diseases, only one defective copy of either gene need be present for nerve cells to die.

From a genetic analysis and an examination of the sequence of the cloned deg-1 gene, applicants disclose that cell death resulted from the production of an abnormal protein that interferes with membranes at the surfaces of the affected nerve cells. As a consequence, the cells swell and burst (lyse).

Applicants also disclose that a third gene, mec-6, is required for the abnormal cell deaths caused by the deg-1 and mec-4 mutations. If the mec-6 gene is defective, neurodegeneration does not occur; in other words, it is suppressed.

Research on suppressor genes like mec-6, on genes that can be mutated to cause cell deaths, and on products encoded by these genes provides new understanding of the molecular processes that lead to neurodegeneration. Furthermore, the mutant animals can be used to screen for drugs that inhibit the neurodegeneration and the cloned genes are used to look to see if similar genes are found in humans.

The *C. elegans* Model

The subject invention is based on genetic studies of a microscopic roundworm called *Caenorhabditis elegans*. *C. elegans* is a particularly useful model for studying neurodegeneration because it allows researchers to observe changes in cells within a living organism over the three days that it takes to develop from a single-cell zygote to a mature adult. These kinds of observations are extremely difficult in other animals and impossible in humans.

Researchers can readily alter the genetic makeup of *C. elegans* and observe the specific effects of the changes in cells and on animal behavior. Through the use of genetic engineering techniques, researchers can characterize mutant genes and the products they encode (e.g., proteins) and their specific effects

*C. elegans* is one of the most thoroughly understood of all multicellular organisms. The biology of its nervous system, which contains 302 neurons, has been well documented. There are several similarities between the *C. elegans* and human nervous systems. For example, many of the *C. elegans*' neurotransmitters, chemicals that nerve cells use to communicate with each other, are the same as human neurotransmitters. In addition, many *C. elegans* genes used both inside and outside of the nervous system have counterparts in mammals. Approximately half of the *C. elegans* genes and proteins that have been characterized to date have structures and functions similar to mammalian genes. These include enzymes, proteins necessary for cell structure, cell surface receptors and genetic regulatory molecules.

The subject invention discloses and characterizes a rare, altered (mutant) form of a gene called deg-1 (degeneration gene-1) that results in an abnormal form of nerve cell death. The deg-1 gene is not involved in the normal process of cell death that ordinarily occurs as part of the animal's growth and development.

The degeneration produced by the deg-1 mutation has parallels to nerve cell loss that occurs in human diseases such as Alzheimer's disease, amyotrophic lateral sclerosis, and Huntington's disease. As in these disorders, the degeneration in some nerve cells is late-onset; something goes awry after neurons develop and mature in apparently normal fashion.

Further, like several human neurodegenerative diseases, the disorder can be inherited from only one parent.

The deg-1 gene is one of three *C. elegans* genes identified disclosed in the subject application that are implicated in neurodegeneration. Three mutations of another gene, called mec-4 (mechanosensory abnormal gene-4), produce similar, neurodegenerative effects on a different set of nerve cells.

Mutations of a third gene, called mec-6, prevent the neurodegeneration induced by the deg-1 and mec-4 mutations. This latter finding indicates that the product of nature (nonmutant) mec-6 gene is required for the abnormal neurodegeneration to occur.

These *C. elegans* genes provide tools for understanding the molecular process of neurodegeneration. Genetic studies to characterize the molecular defect in the deg-1 and mec-4 genes provide an understanding of how the mutant genes cause abnormal neurodegeneration. One can also determine why the product of the mec-6 gene is needed for the degeneration induced by the other genes and what other cellular components may be necessary for this neurodegeneration.

With the DNA structure of the deg-1 gene in hand, scientists can search for similar genes and proteins in humans. Human versions of these genes may lead to diagnostic tests for disorders such as Alzheimer's disease, amyotrophic lateral sclerosis, and Huntington's disease. The products of such genes may provide new, novel targets for developing drugs to treat these severe neurological disorders. Such drugs, that act by binding to these gene products, may interfere directly with the neurodegenerative process.

This invention provides an isolated nucleic acid molecule encoding a wild-type animal protein associated with neuronal degeneration. The invention further provides an isolated nucleic acid molecule encoding a mutated animal protein associated with neuronal degeneration.

The animal is preferably a human being, or the animal may be a nematode, such as *Caenorhabditis elegans*.

In *Caenorhabditis elegans*, the wild-type animal protein may be encoded by the deg-1 gene. Furthermore, the mutated animal protein may be encoded by a mutant of the deg-1 gene, the deg-1 gene having the cDNA sequence shown in FIG. 7. Examples of mutants of the deg-1 gene are designated u38 or uInl.

The wild-type animal protein in *Caenorhabditis elegans* may be encoded by the mec-4 gene. The mutated animal protein may be encoded by a mutant of the mec-4 gene, the mec-4 gene having the cDNA sequence shown in FIG. 9. Examples of mutants of the mec-4 gene are designated e1611, u214, or u231.

This invention also provides an isolated genomic DNA encoding a wild-type animal protein associated with neuronal degeneration, and an isolated genomic DNA encoding a mutated animal protein associated with neuronal degeneration.

This invention further provides a *Caenorhabditis elegans* strain designated TU38 and deposited with the ATCC under Accession No. 40818; a *Caenorhabditis elegans* strain designated TUI191 and deposited with the ATCC under Accession No. 40817; a *Caenorhabditis elegans* strain designated CB1611 and deposited with the ATCC under Accession No. 40820; a *Caenorhabditis elegans* strain designated TU214 and deposited with the ATCC under Accession No. 40819; and a *Caenorhabditis elegans* strain designated TU231 and deposited with the ATCC under Accession No. 40821.

Further provided is a vector which comprises a nucleic acid molecule encoding a wild-type animal protein associated with neuronal degeneration or a nucleic acid molecule encoding a mutated animal protein associated with neuronal degeneration. Suitable vectors includes plasmids, cosmids, and phages.

The isolated nucleic acid molecules of the subject invention may be labeled with a detectable moiety, preferably a radioactive moiety.

The invention further provides a method for detecting a nucleic acid molecule encoding a wild-type protein associated with a degenerative disorder in a human subject which comprises obtaining a sample of DNA or DRNA from the subject, contacting the DNA or mRNA with a nucleic acid molecule encoding a wild-type human protein associated with neuronal degeneration, such nucleic acid molecule being labeled with a detectable moiety, under suitable conditions permitting hybridization of the DNA or mRNA and the nucleic acid molecule, and detecting the hybridized nucleic acid molecules, thereby detecting the nucleic acid molecule encoding the wild-type protein associated with the degenerative disorder.

Further provided is a method for detecting a mutation associated with a degenerative disorder in a human subject which comprises obtaining a sample of DNA or mRNA from the subject, contacting the DNA or mRNA with the nucleic acid molecule encoding a mutated human protein associated with neuronal degeneration, such nucleic acid molecule being labeled with a detectable moiety, under suitable conditions permitting hybridization of the DNA or mRNA and the nucleic acid molecule, and detecting the hybridized nucleic acid molecules, thereby detecting the mutation associated with the degenerative disorder.

This invention also provides a method of detecting a nucleic acid molecule encoding a wild-type protein associated with a degenerative disorder in a human subject which comprises isolating a human subject's mRNA molecules, separating the mRNA molecules, immobilizing the mRNA molecules on a suitable solid support, contacting the immobilized mRNA molecules with a nucleic acid molecule encoding a wild-type human protein associated with neuronal degeneration, such nucleic acid molecule being labeled with a detectable moiety, under suitable conditions permitting hybridization of complementary molecules, detecting the presence of molecules hybridized to sequences on both the first and second nucleic acid sequences and thereby detecting the nucleic acid molecule encoding the wild-type protein associated with the degenerative disorder.

Also provided is a method of detecting a mutation associated with a degenerative disorder in a human subject which comprises isolating a human subject's mRNA molecules, separating the mRNA molecules, immobilizing the mRNA molecules on a suitable solid support, contacting the immobilized mRNA molecules with a nucleic acid molecule encoding a mutated human protein associated with neuronal degeneration, such nucleic acid molecule being labeled with a detectable moiety, under suitable conditions permitting hybridization of complementary molecules, detecting the presence of molecules hybridized to sequences on both the first and second nucleic acid sequences and thereby detecting the mutation associated with the degenerative disorder.

The invention provides a method of detecting a mutation associated with a degenerative disorder in a human subject which comprises isolating a human subject's mRNA molecules, separating the mRNA molecules so obtained by gel electrophoresis, immobilizing the separated mRNA molecules on a suitable solid support, contacting the immobilized mRNA molecules with a nucleic acid molecule encoding a mutated human protein associated with neuronal degeneration, such nucleic acid molecule being labeled with a detectable moiety, under suitable conditions permitting hybridization of complementary molecules, detecting the presence of molecules hybridized to sequences on both the first and second nucleic acid sequences and thereby detecting abnormalities in the subject's mRNA caused by the mutation associated with the degenerative disorder.

Further provided is a method of diagnosing degenerative disease in a human subject which comprises detecting the presence of a mutation associated with a degenerative disorder using the methods disclosed above for detecting a mutation associated with a degenerative disorder.

The subject invention further provides a method of treating a degenerative disease in a human subject which comprises introducing into the human subject an amount of a nucleic acid molecule encoding a wild-type human protein associated with neuronal degeneration effective to suppress neuronal degeneration caused by mutants of the nucleic acid molecule, thereby decreasing neuronal degeneration in the human subject and treating the degenerative disease.

The nucleic acid molecule may be introduced into the human subject by any method known to those skilled in the art, preferably by a vector or in a suitable carrier.

The subject invention also provides a method of causing a diseased human cell to degenerate which comprises introducing a nucleic acid molecule encoding a mutated human protein associated with neuronal degeneration into the diseased human cell so as to cause neuronal degeneration of the diseased human cell, thereby causing the diseased human cell to degenerate.

Examples of diseased human cells include any diseased cells which one would wish to cause to degenerate, such as a cancer cell or a human cell which is infected with the AIDS virus.

The nucleic acid molecule may be introduced into the human subject by any method known to those skilled in the art, preferably by a vector or in a suitable carrier.

The strains of *Caenorhabditis elegans* provided by the subject invention can also be used in a method of screening drugs to identify drugs which prevent or decrease neuronal degeneration which comprises contacting a *Caenorhabditis elegans* strain with a plurality of drugs, determining those drugs which prevent or decrease neuronal degeneration of the strain, and thereby identifying drugs which prevent or decrease neuronal degeneration. Preferably, the *Caenorhabditis elegans* strain is designated TU38, TU1191, CB1611, TU214, or TU231.

The invention further provides a protein encoded by any one of the nucleic acid molecules disclosed herein.

Experimental Details

The dominant mutation deg-1(u38) results in a toxic gene product that leads to the late-onset degeneration of a small number of neurons in the nematode *Caenorhabditis elegans*. Both intragenic and extragenic mutations as well as changes in wild-type gene dosage can delay or block the time of onset of the neuronal deaths. The deg-1 gene has been cloned and a partial complementary (cDNA) reveals that the gene encodes a novel protein with an amino acid sequence similar to that of a membrane receptor. Because the late-onset loss of specific sets of neurons, often as a result of dominant mutations, is characteristic of several human neurodegenerative diseases, the analysis of the deg-1 gene and its suppressors provides a means of understanding the mechanisms underlying some of these human diseases.

The selective degeneration of specific classes of nerve cells is characteristic of the cell death mechanisms of the invention and of many inherited human disorders (1) such as Huntington's disease (2, 3), familial amyotrophic lateral sclerosis (4), familial Alzheimer's Disease (5) and several cerebellar ataxias (6). Many of these diseases are caused by dominant alleles that result in a late-onset degeneration of the affected nerve cells similar to that of the nematode mutants of the invention but their molecular bases are not known. The DNA sequences, nematode mutants and methods of the invention provide unique tools which allow, for the first time, a detailed analysis of neuronal degenerative mechanisms which are characterized by a late-onset degeneration of selective nerve cells.

Applicants have characterized a dominant mutation (u38) of the *C. elegans* gene deg-1 (degeneration), that results in the degeneration of a small set of neurons. One striking feature of some of these deaths is that they have a late onset, occurring long after the neurons form synapses and become functional. The deg-1(u38) mutation results in an abnormal, toxic form of a gene product that is normally non-essential for neuron viability and function. The affected cells swell to many cell diameters and lyse. Without intending to be held to this theory, one possibility for this result is that the deg-1 gene encodes a membrane component, and cell lysis results from compromised membrane integrity. The time of the neuronal degeneration depends upon the level of deg-1(u38) mutant gene activity, which is consistent with an accumulation of a toxic product(s). Mutations in the mec-6 (mechanosensory abnormal) gene suppress the deg-1(u38) neurodegeneration, as well as similar neuronal deaths produced by abnormal, toxic forms of the mec-4 gene product. An understanding of how the mutant deg-1 and mec-4 gene products result in neurodegeneration, and of how normal mec-6 activity is required for this degeneration will provide a basis for methods for preventing or curing neurodegenerative disorders in humans.

The deg-1(u38) phenotype

The deg-1(u38) mutant was identified in a screen for touch-insensitive mutants following ethyl methanesulfonate (EMS) mutagenesis at 25° C. The gene is located on the X chromosome (see legend to FIG. 1). The deg-1(u38) animals differ from other touch-insensitive mutants (8) in that although both types of mutants are insensitive to the gentle touch of a hair, only the deg-1 mutants are insensitive to the more severe prod of a thin wire. They are also insensitive only at the tail. This more severe phenotype (designated Tab for Touch abnormal) suggests a defect in the two PVC interneurons, which receive synaptic inputs from posterior touch receptor neurons (9). The PVC cells degenerate in these mutants. A similar behavioral abnormality results from laser ablation of the PVC cells in wild-type animals.

Although the PVC cells arise during embryogenesis (10), deg-1 mutants are touch-sensitive at hatching and become Tab later, during the second and third larval stages (L2 and L3) at 25° C. (FIG. 1). The stage of onset of touch insensitivity is delayed further when animals are grown at lower temperatures, so mutants grown at 15° C. become Tab as gravid adults.

Virtually all deg-1 animals, when viewed by Nomarski microscopy (11), have one or two degenerating cells near the normal position of the PVC cells, 24 hours after hatching at 25° C. (FIG. 2). The degeneration is first seen as a small vacuole that surrounds the nucleus. This vacuole, which contains particles displaying Brownian motion, enlarges by several cell diameters over the next few hours, during which the nucleus disintegrates.

This degeneration differs from programmed cell death, a common feature in *C. elegans* development, in which affected cells become refractile and condensed as they die (11). Here we use the term degeneration for the type of death seen in deg-1(u38) mutants to distinguish it from the morphologically distinct programmed cell death. The deg-1(u38) degeneration phenotype (termed Deg) has been seen in animals with dominant mutations of the gene mec-4 [mec-4(d)]. Dominant, but not recessive, mec-4 mutations result in the degeneration of the touch receptor neurons (8), probably by the production of a toxic product that is expressed within the touch receptor neurons (12). As in deg-1(u38) animals, some of the affected cells in mec-4(d) mutants display a late-onset degeneration (8, 13).

Other classes of neurons, unrelated by position, lineage, or function to each other or to the PVC cells also degenerate at various times during development in deg-1(u38) mutants (FIG. 2). Although all of the animals become Tab and must have one or two degenerating PVC cells at 24 hours at 25.C, the pattern of these other deaths varies considerably (FIG. 2 legend). Without intending to be held to this theory, one explanation is that this variability reflects incomplete penetrance of the Deg phenotype for each cell or variations in the times of onset or duration of the degenerations.

The deg-1 mutants also contain empty vacuoles (vacuoles not associated with nuclei) at the tip of the nose, along the ventral cord, and in the tail (FIG. 2), especially in newly hatched animals. They may be located in the hypodermis (epidermis).

Genetic characterization

Alleles like u38 are extremely rare, and no similar deg-1 mutation has been isolated prior to that of the invention. The original u38 mutant was isolated in a screen of progeny representing 70,000 copies of the gene. Such rarity [loss-of-function mutations in $C.$ $elegans$ arise at a frequency of about $5 \times 10^{-4}$ (14, 15)] and the dominant Deg and Tab phenotypes suggest that u38 is not a deg-1 null mutation. Indeed, loss of deg-1 function gives rise to no detectable abnormal phenotype (the animals appear wild-type).

The u38 animals can readily be reverted to a wild-type phenotype. As 24 of 25 non-Tab (touch sensitive) revertants obtained by EMS mutagenesis have not segregated Tab animals, these reverting mutations are presumed to be intragenic. (The remaining revertant strain produces some Tab progeny but with an unusual segregation pattern and has not been studied further.) Three additional intragenic revertants arose spontaneously from a mut-2; deg-I double mutant (the mut-2 mutation often activates transposons in $C.$ $elegans$ (16)). Most of the suppressor mutations, including those obtained in the mut-2 background, seem to revert or almost to completely the Tab and Deg phenotypes, and all but one are recessive to the u38 mutation. The frequency at which the intragenic suppressor mutations arose with EMS mutagenesis ($4 \times 10^{-4}$) is similar to that found for loss-of-function mutations in other $C.$ $elegans$ genes (14, 15). Without intending to be held to this conclusion, the molecular analysis below also supports the conclusion that disruption of the deg-1 gene leads to a wild-type null phenotype.

In one embodiment, the mutant deg-1 revertant of the invention does not produce a detectable phenotype. In an additional embodiment, the mutant deg-1 gene encodes an abnormal gene product. In a preferred embodiment, the abnormal deg-1 gene product interferes with normal cell homeostasis.

The invention is meant to include wild-type and mutant deg-1 gene products and alleles thereof and other genes which may be described as a deg-1 gene family, that is, genes which are highly homologous to deg-1 and encode proteins which have similar amino acid sequences and functions to the deg-1 gene cloned herein. The invention further includes the proteins encoded by such genes.

Two of the intragenic suppressor mutations, u352 and u354, only partially suppress the effects of u38. They delay the onset of the Tab phenotype, by almost 24 and 48 hours at 25° C. for u354 and u352, respectively (FIG. 3). The PVC deaths are also seen later, the cells dying in young and old adults, respectively. The various deaths caused by the u38 mutation may be unequally affected by these suppressor mutations; in particular the u352 mutation seems to have its most pronounced effect on the PVC death (FIG. 3).

Additional copies of the wild-type gene delay, although to a smaller degree than temperature or intragenic mutations, the onset of the u38 Tab phenotype (FIG. 4). In general, the delay in the onset of the Tab phenotype increases in proportion to the ratio of wild-type to the mutant allele. In a highly preferred embodiment, cell death is delayed by providing the wild-type gene which corresponds to the mutant cell-death-inducing gene to the mutant cell.

Independence of deg-1(u38) degenerations

The deg-1 degenerations differ from programmed cell deaths not only morphologically, but also genetically. Mutations that prevent all programmed cell deaths in $C.$ $elegans$ hermaphrodites [ced-3(n717) and ced-4(n1162); (19)], did not prevent the deg-1 degenerations. In fact, ced-3; deg-1(u38) and ced-4; deg-1(u38) double mutants had additional degenerations in the head at hatching (total deaths with ced-3: $4.0 \pm 0.4$; with ced-4: $4.6 \pm 0.6$; n=25; mean±s.e.m., n=25 for each; deg-1(u38) mutants alone have $2.2 \pm 0.2$ deaths, n=20). In one embodiment, extra cells that normally survive in ced-3 and ced-4 animals live and then degenerate in the corresponding deg-1 double mutant.

Late-onset degeneration of the PVC cells may be triggered by larval cell interactions, including, but not limited to, the initation of aberrant differentiation and/or the toxic stimulation of the cells, as in, for example, glutamate neurotoxicity (21). Many neurons arise postembryonically in $C.$ $elegans,$ but they do not seem to be required for the PVC deaths, as the double mutant lin-6(e1466); deg-1(u38), in which none of these cells are made (22, 23), is Tab. Moreover, the elimination of the touch receptor neurons, which synapse onto the PVC cells, by the addition of the unc-86(e1416) mutation (8) had no effect in the deg-1 deaths. Thus, neither postembryonically-derived targets nor a major input to the PVC cells is required for these deaths. Therefore, in a preferred embodiment, the deg-1(u38) mutation may act in a cell-autonomous fashion. In another embodiment, the cell interactions trigger a deg-1-dependent degeneration.

Suppression by mec-6 mutations

Mutations in the mec-6 gene suppress the degenerations caused by both the mec-4(d) and deg-1(u38) mutations. This result not only indicates an underlying genetic similarity in the deaths caused by these mutations, but also identifies a gene, mec-6, whose activity is required for the neurodegenerative process. The effect on the mec-4(d) mutations was discovered through the construction of a set of double mutants, each containing a mec-4(d) mutation and a mutation in one of the other genes required for touch receptor function (7) to determine whether any of these mutations could prevent the mec-4(d) deaths. [Previous experiments (8) showed that mutations in genes required for the generation of the touch receptors or for the specification of their differentiation prevent the appearance of the mec-4(d)-dependent deaths.] Mutations in the genes mec-1, mec-2, mec-6 to mec-10, mec-12, mec-14, mec-17 and mec-18 were tested, but only mec-6 mutations suppressed the mec-4(d) degenerations. Although the animals remained touch insensitive (the mec-6 phenotype), the touch cells did not die. In fourteen mec-6; mec-4(d) strains were made using eight mec-6 alleles and the three mec-4(d) mutations, all had normal appearing adult touch cells. The mec-6 mutations suppressed only when homozygous. The mec-6 mutation u247 results in a temperature-sensitive phenotype for touch sensitivity (7). Suppression of the mec-4(d) degenerations by u247 is also temperature sensitive; deaths were seen in newly-hatched larvae at 15° C., but not at 25° C. (it was not possible to delay the onset of these deaths in temperature-shift experiments). Thus, in a preferred embodiment the loss of mec-6 activity results in suppression. In another embodiment, the production of an allele-specific product results in the suppression. As other features of the touch receptors seem unaffected in mec-6 mutants (7, 8), the wild-type mec-6 product is probably required for neurodegeneration induced by the abnormal products of the mec-4(d) alleles.

Mutations in mec-6 (u41, u247 and u450 were used) also suppress the effects of deg-1(u38). Double mutants are insensitive to the touch of hair at both head and tail (the mec-6 phenotype), but they are not Tab. Moreover, the mec-6 mutations seem to suppress all of the deg-1-induced deaths (no vacuolated cells were seen in any newly-hatched larvae) as well as the appearance of the presumptive hypodermal vacuoles (FIG. 2D). As with the suppression of the mec-4(d) deaths, suppression only occurred in mec-6 homozygotes. Suppression of deg-1 by mec-6 indicates that mec-6 expression is not restricted to the touch system, even though the only detectable behavioral phenotype of mec-6 mutants is touch insensitivity. Without intending to be held to this conclusion, the absence of a Tab phenotype in mec-6 mutants suggests that deg-1 in the PVC cells is not replaced by the activity of other deg-1 like genes, at least not those requiring mec-6 function.

Molecular Analysis of deg-1

The deg-1 gene was cloned by transposon tagging, utilizing the mut-2-derived revertants (FIG. 5). DNA flanking the insertion site of the transposon Tc1 hybridized to C47C12 (FIG. 6), a cosmid clone adjacent to a cosmid containing the mec-7 gene (24, 25), a position consistent with the genetic mapping of deg-1 (FIG. 1 legend). Hybridization with C47C12 revealed insertions in one other mut-2-derived revertant and a possible deletion in one EMS-derived revertant (FIG. 5). Further evidence that the transposon insertions are in the deg-1 gene came from experiments in which the transposon-containing strains were themselves reverted by reintroducing the mut-2 mutation. This reversion with the reappearance of the Deg and Tab phenotypes was accompanied by the excision of the transposon (FIG. 5).

Two partial deg-1 cDNAs were isolated from a λgt10 library with cDNAs from 12-hour old larvae, provided by J. Ahringer and J. Kimble (University of Wisconsin). Similar libraries may be constructed using techniques known in the art (for example, see: Maniatis, T. et al., *Molecular Cloning (A Laboratory Manual)*, 2nd edition, Cold Spring Harbor Laboratory, 1989) and custom cDNA or genomic library construction may also be obtained commercially (for example, with Promega Corporation, Madison, Wisc.). As the transposon is inserted in the revertant u38u478 resides in a 187-bp region that contains sequences in the cDNAs surrounding a 50-bp intron (FIG. 6 legend), it is likely that these cDNAs represent deg-1 transcripts. The larger cDNA encodes an open reading frame of 884 base pairs (bp) (FIG. 7) followed by 141 bp and a poly(A) tail. The smaller cDNA lacks 72-bp from within the open reading frame. As no untranslated sequence precedes these open reading frames, the cDNAs seem to be incomplete. The inferred polypeptide sequence of 294 amino acids from the larger cDNA, which is not strongly homologous to other DNA and protein database entries, has three notable features: (1) a hydrophobic region from residues 215–255; (2) two possible sites for N-linked glycosylation (26) located at positions 8 and 122; and (3) a cysteine-rich region, containing 13 of the 14 cysteines in the sequence, between positions 66 and 187. The 72 bp absent in the smaller cDNA encode 24 amino acids in the cysteine-rich region (including two cysteines) and could represent an alternatively-spliced variant.

The structure of the deg-1 product is consistent with its being a membrane protein. The hydrophobic domain has an uninterrupted stretch of 17 amino acids, which is sufficient to span the lipid bylayer (27), and an additional 24 amino acids, only three of which are charged. This structure but not sequence, is also found in the predicted membrane spanning domain of the B subunit of the T-cell receptor (28, 29). It is possible that the extended hydrophobic region of the deg-1 product (including the charged residues) is submerged in the cell membrane, and may interact with analogous domains of other membrane proteins. The localization of the large number of cysteines, a feature of several receptor proteins (30–33), and the two N-linked glycosylation sites in the N-terminal region, is consistent with this region being an extracellular domain (FIG. 7).

Figure 5B:
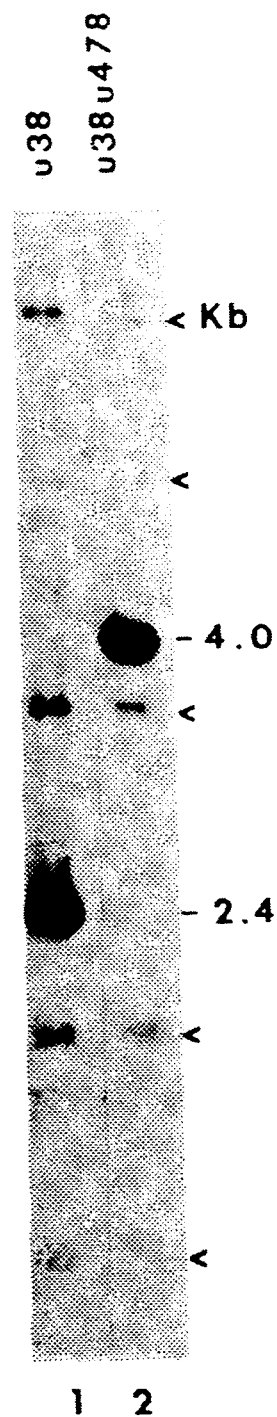

The molecular analysis supports the hypothesis derived from our genetic studies that deg-1 may be a member of a gene family. The cDNAs as well as a genomic DNA fragment to which they bind (the IC fragment; FIG. 6) hybridize to several genomic fragments (FIG. 5b).

The wild-type deg-1 gene, as defined by the restriction fragments that differ in the u38 revertants or that hybridize with the cDNAs, is contained within a 35 kilobase (kb) BamHI fragment (FIG. 6). The corresponding fragment cloned from the dominant allele deg-1(u38) (FIG. 6, TU#3), when transformed into wild-type animals, produces both the Tab and Deg phenotypes (FIG. 6 legend). In a highly preferred embodiment, stable cell lines are identified which possess copies of the transformed DNA attached to, or inserted within, the genomic DNA in a manner which is stably inherited from generation to generation. It is highly desirable to identify such stable transformant cell lines. Transformant lines may be unstable if the DNA is not attached or otherwise integrated into the host's chromosomal DNA. Especially, those transformants which possess extrachromosomal arrays of the injected DNA may be genetically unstable. However, in one strain (uIn1) the mutant phenotypes are stably inherited, and karyotype and Southern blot analysis indicate that at least ten intact copies of the transformed DNA have attached to the X chromosome.

The uIn1 animals resemble u38 mutants, but display some differences. The PVC neurons degenerate at essentially the same time in both strains (data not shown), but more degenerating cells are seen in the head during the second larval stage (L2) in the transformed animals [0.5±0.0 deaths in u38 (n=21) and 3.7±0.2 in uIn1 (n=9)]. The extra copies of deg-1(u38) DNA or its misexpression in the transformants may cause additional cells to die or change the onset of some cell degeneration. Unlike the situation in u38 mutants, the Deg and Tab phenotypes of uInl animals are not completely suppressed by mec-6 mutations u450 and e1342. The head degenerations in mec-6; uInl strains are suppressed, but the PVC degenerations occur in many of the animals (8 of 28 late L2 mec-6; uInl larvae had these deaths compared with 7 of 20 uInl larvae of the same age). Most mec-6; uInl adults are Tab. Hence, some deg-1-dependent degenerations do not absolutely require wild-type mec-6 function, at least under these conditions of increased copies of the u38 DNA.

Discussion

Dominant mutations of deg-1 and mec-4 cause the degeneration of a small number of neurons. Although different cells die in the deg-1 and mec-4 mutants, these mutations cause an apparently similar cell death that differs morphologically and genetically from programmed cell death. The degeneration results from the expression of alleles that seem to encode abnormal products; the wild-type genes are not needed for cell viability. The dominant mutations are suppressed by mec-6 mutations, suggesting that similar molecular processes may underlie these neuronal degenerations. Over 420 mutations (many of them dominant) in eighteen genes needed for touch receptor development and function have been identified, yet only the three mec-4(d) mutations cause the deaths of the touch cells (7), and no other mutations are known that mimic the deg-1(u38) mutation. (This is not the only type of abnormal cell death seen in *C. elegans*; mutations in egl-1 (34), lin-24 (35), and lin-33 (35) seem to produce ectopic cell deaths.)

An intriguing feature of the deg-1(u38) phenotype is the late onset of cell degeneration of many of the affected cells. Because the loss of the PVC cells results in a detectable phenotype, the behavioral defect in these animals also seems to be of late onset, even though other cells have died earlier. The PVC degenerations can occur in animals of different ages (from second stage larvae to egg-laying adults) depending on the nature of the mutation, the growth temperature, and the dosage of the wild-type gene. Without intending to be held to this theory, these data suggest that the degenerative phenotype is not directly coupled to a specific, developmental event, such as the appearance or maturation of a particular set of cells, a conclusion supported by the observations that the deg-1-dependent PVC deaths are not affected when various synaptic targets and inputs have been eliminated genetically. More likely, these data suggest that the accumulation of a mutant product leads to the degeneration phenotype. Certainly, a particular time of onset cannot be taken as a characteristic feature of the Tab phenotype. Such may also be true of human diseases. For example, the study of restriction fragment length polymorphisms linked to the Huntington's disease gene suggested that mutant alleles of the same genetic locus may give rise to diseases with different times of onset (36).

Membrane proteins which have similar structures to the deg-1 protein of the invention include ion channels and membrane-bound receptors. An abnormal product from a dominant mutation might prove toxic if, directly or indirectly, it compromised membrane integrity. Several observations suggest that chemically open membrane channels can lead to cell lethality. The continued opening of acetylcholine channels at the neuromuscular junction, for example, leads to localized degeneration of the endplate because of the activation of calcium-dependent proteases (37), and sustained opening of capsaicin-sensitive channels in putative pain receptor neurons can cause lysis through osmotic imbalance and calcium influx (38). The osmotic disruption and calcium entry that result from glutamate neurotoxicity (39) may also result from a similar mechanism. The partial sequence of the deg-1 product is consistent with a role in membrane function, although it is not homologous to known channel proteins. The deg-1 product could affect membrane integrity indirectly. For example, the mutant product might bind to a channel or other membrane component and modify its activity. Of relevance may be a mammalian protein with only one apparent transmembrane domain that confers novel channel properties on Xenopus oocytes (40, 41). Alternatively, deg-1 may encode a ligand-activated receptor. The cysteine-rich extracellular domain suggests such a function. The u38 phenotype could then arise from an inappropriate activation of a second messenger pathway that alters the activity of membrane proteins. A further possibility is that the deg-1(u38) sized for the abnormal catabolism of the β-amyloid precursor protein in Alzheimer's disease (42).

The suppression of deaths by mec-6 mutations indicates an important role for mec-6 in neurodegeneration. This mec-6 activity could be required for the mec-4(d) and deg-1 degenerations either because it activates the products of these genes (perhaps by regulating their synthesis or subcellular localization) or because it is a necessary target (such as a channel) or cofactor for their action. In all these cases, loss of mec-6 activity would prevent the neuronal degeneration. The further molecular analysis of the deg-1, mec-4, and mec-6 9enes as well as the localization of their products will be important in elucidating the ways these genes act.

The selective degeneration of particular sets of neurons is characteristic of a number of human genetic diseases (1). Many late-onset human neurodegenerative diseases are expressed as dominant traits (1), and although many more dominant human genetic diseases are known than recessive or X-linked ones (43), the proportion of dominant, late-onset diseases of the nervous system is particularly high. Another similarity between the *C. elegans* degenerations and those in human diseases is their appearance. It is difficult to determine whether the pathologies described for the human diseases are identical to the vacuolated deaths seen in the *C. elegans* mutants. Yet in humans, vacuolated cortical cells ("ballooned neurons") occur in some patients with neurodegenerative diseases, including instances of Alzheimer's disease (44), and vacuolated cells have been reported in two cases of motor neuron disease (45, 46). Vacuolization is also seen in genetically induced neuronal death in several mouse mutants (47–49).

Although the mec-4(d) and deg-1-induced degenerations are distinct from programmed cell deaths in *C. elegans*, mechanisms similar to those occurring in these mutants may function not only in neurodegenerative diseases, but also in cell deaths that arise during normal development in other organisms. Several researchers have reported that some, but not all naturally-occurring neuronal deaths in vertebrates are characterized by an initial dilation and vacuolization of the cytoplasm of the affected cells (50, 53). The process of cell death in these instances may be similar to the *C. elegans* degenerations. Such cell death could, as with the PVC cells in deg-1(u38) mutants, exhibit delayed onset. Such a process may occur in the death of the subplate neurons of the mammalian cerebral cortex die with a vacuolated appearance after making functional embryonic synapses (54, 55). It seems likely that cell death during normal development occurs through more than one mechanism, one of which could utilize a deg-1(u38)- or mec-4(d)-like product.

This invention comprises genetic sequences coding for the deg-1 gene, the mec-6 gene and the mec-4 gene, mRNA or antisense mRNA, expression vehicles containing the genetic sequences for these genes, hosts transformed therewith and recombinant protein and antisense RNA produced by such transformed host expression. The invention further comprises antibodies directed against the proteins.

The process for genetically engineering the proteins of the invention is facilitated through the cloning of genetic sequences which are capable of encoding the proteins and through the expression of such genetic sequences. As used herein, the term "genetic sequences" is intended to refer to a nucleic acid molecule (preferably DNA). Genetic sequences which are capable of encoding the proteins of the invention are derived from a variety of sources. These sources include genomic DNA, cDNA, synthetic DNA, and combinations thereof.

The DNA which encodes the proteins of the invention may or may not include naturally-occurring introns. Moreover, such genomic DNA may be obtained in association with the 5' promoter region of the gene sequences and/or with the 3' transcriptional termination region. Further, such genomic DNA may be obtained in association with the genetic sequences which encode the 5' non-translated region of the mRNA and/or with the genetic sequences which encode the 3' non-translated region. To the extent that a host cell can recognize the transcriptional and/or translational regulatory signals associated with the expression of the mRNA and protein, then the 5' and/or 3' non-translated regions of the native gene, and/or, the 5' and/or 3' non-translated regions of the mRNA, may be retained and employed for transcriptional and translational regulation. Genomic DNA can be extracted and purified from any cell of the species by means well-known in the art (for example, see *Guide to Molecular Cloning Techniques*, S. L. Berger et al., eds., Academic Press (1987).) Alternatively, mRNA which encodes the proteins of the invention can be isolated from any cell which produces or expresses such proteins and used to produce cDNA by means well-known in the art (for example, see *Guide to Molecular Cloning Techniques*, S. L. Berger et al., eds., Academic Press (1987).) Preferably, the mRNA preparation used will be enriched in mRNA coding for the proteins of the invention, either naturally, by isolation from cells which are producing large amounts of the protein, or in vitro, by techniques commonly used to enrich mRNA preparations for specific sequences, such as sucrose gradient centrifugation, or both.

For cloning into a vector, such suitable DNA preparations (either human genomic DNA or cDNA) are randomly sheared or enzymatically cleaved, respectively, and ligated into appropriate vectors to form a recombinant gene (either genomic or cDNA) library. A DNA sequence encoding the proteins of the invention or functional derivatives thereof may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well-known in the art.

Libraries containing clones encoding the proteins of the invention may be screened and a desired clone identified by any means which specifically selects for that protein's DNA such as, for example, (a) by hybridization with an appropriate nucleic acid probe(s) containing a sequence specific for the DNA of this protein; or (b) by hybridization-selected translational analysis in which native mRNA which hybridizes to the clone in question is translated in vitro and the translation products are further characterized; or (c) if the cloned genetic sequences are themselves capable of expressing mRNA, by immunoprecipitation of a translated protein product produced by the host containing the clone.

Oligonucleotide probes specific for the proteins of the invention which can be used to identify clones to these proteins can be designed from knowledge of the amino acid sequence of the protein.

Because the genetic code is degenerate, more than one codon may be used to encode a particular amino acid (Watson, J. D., in: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D. in: *Molecular Biology of the Gene*, 3rd Ed., W. A. Benjamin, Inc., Menlo Park, Calif. (1977)), one or more different oligonucleotides can be identified from the amino acid sequence, each of which would be capable of encoding the proteins of the invention. The probability that a particular oligonucleotide will, in fact, constitute the actual protein sequence can be estimated by considering abnormal base pairing relationships and the frequency with which a particular codon is actually used (to encode a particular amino acid) in eucaryotic cells. Such "codon usage rules" are disclosed by Lathe, R., et al., J. Molec. Biol. 183: 1–12 (1985). Using the "codon usage rules" of Lathe, a single oligonucleotide sequence, or a set of oligonucleotide sequences, that contain a theoretical "most probable" nucleotide sequence capable of encoding the desired sequence is identified.

The suitable oligonucleotide, or set of oligonucleotides, which is capable of encoding a fragment of the protein's gene (or which is complementary to such an oligonucleotide, or set of oligonucleotides) may be synthesized by means well-known in the art (see, for example, *Synthesis and Application of DNA and RNA*, S. A. Narang, ed., 1987, Academic Press, San Diego, Calif.) and employed s a probe to identify and isolate the gene by techniques known in the art. Techniques of nucleic acid hybridization and clone identification are disclosed by Maniatis, T., et al. in *Molecular Cloning, A Laboratory Manual*, Cold Spring Harbor Laboratories, Cold Spring Harbor, N.Y. (1982)), and by Hames, B. D., et al. in *Nucleic Acid Hybridization, A Practical Approach*, IRL Press, Washington, D.C. (1985)), which references are herein incorporated by reference. Those members of the above-described gene library which are found to be capable of such hybridization are then analyzed to determine the extent and nature of the protein encoding sequences which they contain.

To facilitate the detection of the desired clone, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., J. Mol. Biol. 113: 237 (1977) and by T4 DNA polymerase replacement synthesis as described in, for example, Deen, K. C., et al., Anal. Biochem. 135: 456 (1983).

Alternatively, polynucleotides are also useful as nucleic acid hybridization probes when labeled with a non-radioactive marker such as biotin, an enzyme or a fluorescent group. See, for example, Leary, J. J., et al., Proc. Natl. Acad. Sci. USA 80: 4045 (1983); Renz, M., et al., Nucl. Acids Res. 12 3435 (1984); and Renz, M., EMBO J. 6: 817 (1983).

Thus, in summary, the actual identification of sequences encoding the proteins of the invention permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the gene.

In an alternative way of cloning a gene encoding the proteins of the invention, a library is prepared using an expression vector, by cloning DNA or, more preferably cDNA prepared from a cell capable of expressing the desired protein, into an expression vector. The library is then screened for members which express the desired protein, for example, by screening the library with antibodies to the protein.

The above discussed methods are, therefore, capable of identifying genetic sequences which are capable of encoding the proteins of the invention or fragments of this protein. In order to further characterize such genetic sequences, and, in order to produce the recombinant protein, it is desirable to express the proteins which these sequences encode. Such expression identifies those clones which express proteins possessing characteristics of the proteins of the invention. Such characteristics may include the ability to specifically bind antibody to the proteins, the ability to elicit the production of antibody which is capable of binding to the protein, the ability to provide a protein-specific function to a recipient cell, among others.

To express the recombinant proteins of the invention, transcriptional and translational signals recognizable by an appropriate host are necessary. The cloned protein encoding sequences, obtained through the methods described above, and preferably in a double-stranded form, may be operably linked to sequences controlling transcriptional expression in an expression vector, and introduced into a host cell, either procaryote or eucaryote, to produce recombinant protein or a functional derivative thereof. Depending upon which strand of the protein encoding sequence is operably linked to the sequences controlling transcriptional expression, it is also possible to express protein antisense RNA or a functional derivative thereof.

Expression of the protein in different hosts may result in different post-translational modifications which may alter the properties of the protein. Preferably, the present invention encompasses the expression of the protein, or a functional derivative thereof, in eucaryotic cells, and especially mammalian, insect and yeast cells. Especially preferred eucaryotic hosts are mammalian cells neural cells, either in vivo or in tissue cultue. Mammalian cells provide post-translational modifications to recombinant proteins which include folding and/or glycosylation at sites similar or identical to that found for the native protein.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two DNA sequences does not (1) result in the introduction of a frame-shift mutation; (2) interfere with the ability of the expression regulatory sequences to direct the expression of the protein's mRNA, antisense RNA, or protein; or (3) interfere with the ability of the protein's template to be transcribed by the promote region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene.

Expression of the proteins of the invention in eucaryotic hosts requires the use of regulatory regions functional in such hosts, and preferably eucaryotic regulatory systems. A wide variety of transcriptional and translational regulatory sequences can be employed, depending upon the nature of the eucaryotic host. The transcriptional and translational regulatory signals can also be derived from the genomic sequences of viruses which infect eucaryotic cells, such as adenovirus, bovine papilloma virus, Simian virus, herpes virus, or the like. Preferably, these regulatory signals are associated with a particular gene which is capable of a high level of expression in the host cell. Vectors may also be designed which possess the ability to target certain cells, such as neuronal cells, and which cross the blood-brain barrier. For example, a mutant retroviral vector may be used if such a vector is designed to by non-transforming or otherwise harmful to the host cell, and if it retains an ability to transport across the blood-brain barrier and infect neuronal target cells.

In eucaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA product capable of translation are preferred, and especially, strong promoters such as the promoter for actin, collage, myosin, etc., can be employed provided they also function as promoters in the host cell. Preferred eucaryotic promoters include the promoter of the mouse metallothionein I gene (Hamer, D., et al., J. Mol. Appl. Gen. 1: 273–288 (1982)); the TK promoter of herpes virus (McKnight, S., et al., Cell 31: 355–365 (1982)); the SV40 early promoter (Benoist, C., et al., Nature (London) 290: 304–310 (1981)); in yeast, the yeast gal4 gene promoter (Johnston, S. A., et al., Proc. Natl. Acad. Sci. (USA) 79: 6971–6975 (1982); Silver, P. A., et al., Proc. Natl. Acad. Sci. (USA) 81: 5951–5955 (1984) or a glycolytic gene promoter may be used.

As is widely known, translation of eucaryotic mRNA is initiated at the codon which encodes the first methionine. For this reason, it is preferable to ensure that the linkage between the eucaryotic promoter and a DNA sequence which encodes the protein of the invention, or a functional derivative thereof, does not contain any intervening codons which are capable of encoding a methionine. The presence of such codons results either in a formation of a fusion protein (if the AUG codon is in the same reading frame as the protein's DNA sequence) or a frame-shift mutation (if the AUG codon is not in the same reading frame as the encoding sequence).

If desired, a fusion product of the protein may be constructed. For example, the sequence coding for the protein may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

Transcriptional initiation regulatory signals can be selected which allow for repression or activation, so that expression of the operably linked genes can be modulated. Of interest are reglatory signals which are temperature-sensitive so that by varying the temperature, expression can be repressed or initiated, or are subject to chemical regulation, e.g., metabolite. Also of interest are constructs wherein both the protein mRNA and antisense RNA are provided in a transcribable form but with different promoters or other transcriptional regulatory elements such that induction of protein mRNA expression is accompanied by repression of antisense RNA expression, and/or, repression of protein mRNA expression is accompanied by induction of antisense RNA expression. Translational signals are not necessary when it is desired to express protein antisense RNA sequences.

If desired, the non-transcribed and/or non-translated regions 3' to the sequence coding for the desired protein can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eucaryotic cells. Where the native expression control sequence signals do not function satisfactorily in the host cell, then sequences functional in the host cell may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the protein DNA construct into the host cell chromosomal DNA, or to allow it to exist in an extrachromosomal form.

If the DNA encoding sequence and an operably linked promoter is introduced into a recipient eucaryotic cell as a nonreplicating DNA (or RNA) molecule, which may either be a linear molecule or, more preferably, a closed covalent circular molecule which is incapable of autonomous replication, the expression of the protein may occur through the transient expression of the introduced sequence.

In a preferred embodiment, genetically stable transformants may be constructed with vector systems, or transformation systems, whereby a desired protein's DNA is integrated into the host chromosome. Such integration may occur de novo within the cell or, in a most preferred embodiment, be assisted by transformation with a vector which functionally inserts itself into the host chromosome, for example, with retroviral vectors, transposons or other DNA elements which promote integration of DNA sequences in chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by cotransfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eucaryotic plasmids include those derived from the bovine papilloma virus, vaccinia virus, SV40, and, in yeast, plasmids containing the 2-micron circle, etc., or their derivatives. Such plasmids are well-known in the art (Botstein, D., et al., Miami Wntr. Symp. 19: 265-274 (1982); Broach, J. R., in *The Molecular Biology of the Yeast Saccharomyces: Life Cycle and Inheritance*, Cold Spring Harbor Laboratory, Cold Spring Harbor, N.Y., pp. 445-470 (1981); Broach, J. R., Cell 28: 203-204 (1982); Bollon, D. P., et al., J. Clin. Hematol. Oncol. 10: 39-48 (1980); Maniatis, T. in *Cell Biology: A Comprehensive Treatise, Vol. 3. Gene Expression*, Academic Press, N.Y., pp. 563-608 (1980)), and are commercially available. For example, mammalian expression vector systems which utilize the MSV-LTR promoter to drive expression of the cloned gene, and in which it is possible to cotransfect with a helper virus to amplify plasmid copy number, and, integrate the plasmid into the chromosomes of host cells have been described (Perkins, A. S. et al., Mol. Cell Biol. 3: 1123 (1983); Clontech, Palo Alto, Calif.).

Once the vector or DNA sequence containing the construct(s) is prepared for expression, the DNA construct(s) is introduced into an appropriate host cell by any of a variety of suitable means, including transfection. After the introduction of the vector, recipient cells are grown in a selective medium, which selects for the growth of vector-containing cells. Expression of the cloned gene sequence(s) results in the production of the desired protein, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein is isolated and purified in accordance with conventional conditions, such as extraction, precipitation, chromatography, affinity chromatography, electrophoresis, or the like, by means well-known in the art.

The protein encoding sequences of the invention, obtained through the methods above, will provide sequences which by definition, encode a desired protein and which may then be used to obtain antisense RNA genetic sequences as the antisense RNA sequence will be that sequence found on the opposite strand of the strand transcribing the peptide sequence's mRNA. The antisense DNA strand may also be operably linked to a promoter in an expression vector such that transformation with this vector results in a host capable of expression of an antisense RNA in the transformed cell. Antisense RNA and its expression may be used to interact with an endogenous DNA or RNA in a manner which inhibits or represses transcription or translation of the gene or mRNA respectively in a highly specific manner. Use of antisense RNA probes to block gene expression is discussed in Lichtenstein, C., Nature 333: 801-802 (1988). Such antisense RNA may be useful in the therapeutic treatments of the invention.

REFERENCES

1. Adams, R. D., and Victor, M. in *Principles of Neurology*, 3rd edition, McGraw Hill, N.Y., Ch. 42, pages 859-901 (1985).
2. Hayden, M. R., Huntington's Chorea, Springer-Verlag, Berlin (1981).
3. Gusella et al., Nature 306: 234-238 (1983).
4. Mulder, D. W., Kurland, L. T., Offord, K. P., and Beard, M., Neurol. 36: 511-517 (1986).
5. Davies, P., Neurobiol. Aging 7: 459-466 (1986).
6. Harding, A. E. in Hereditary Ataxias and Related Disorders, Churchill Livingstone, Edinburgh, Ch. 10, pages 129-165 (1984).
7. Chalfie, M. and Au, M., Science 243: 1027-1033 (1989).
8. Chalfie, M., and Sulston, J., Devl. Biol. 82: 358-370 (1981).
9. Chalfie, M. et al., J. Neurosci. 5: 956-964 (1985).
10. Sulston, J. E., Schierenberg, E., White, J. G., and Thomson, J. N., Develop. Biol. 100: 64-119 (1983).
11. Sulston, J. E., and Horvitz, H. R., Devl. Biol. 56: 110-156 (1977).
12. Herman, R. K., Genetics 116: 377-388 (1987).
13. Way, J. C. and Chalfie, M., Genes Devl. 3: 1823-1833 (1989).
14. Brenner, S., Genetics 77: 71-94 (1974).
15. Greenwald, I. S., and Horvitz, H. R., Genetics 96: 147-164 (1980).
16. Collins, J., Saari, B., and Anderson, P., Nature 328: 726-728 (1987).
17. Suzuki, D. T., Science 170: 695-706 (1970).
18. Ferguson, E. L., and Horvitz, H. R., Genetics 123: 109-121 (1989).
19. Ellis, H. M., and Horvitz, H. R., Cell 44: 817-829 (1986).
20. Avery, L., and Horvitz, H. R. Cell 51: 1071-1078 (1987).
21. Choi, D., Neuron 1: 623-634 (1988).
22. White, J. G., Albertson D. G., and Anness, M. A., Nature 271: 764-766 (1978).
23. Sulston, J. E., and Horvitz, H. R., Devl Biol. 82: 41-55 (1981).
24. Coulson, A., Sulston, J., Brenner, S., and Karn, J., Proc. Natl. Acad. Sci. USA 83: 7821-7825 (1986).
25. Savage, C., et al., M., Genes & Devl. 3: 870-881 (1989).
26. Hubbard, S. C. and Ivatt, R. J., Ann. Rev. Biochem. 50: 555-583 (1981).
27. Adams, G. A. and Rose, J. K., Cell 41: 1007-1015 (1985).
28. Yanagi, Y., et al., Nature 308: 146-149 (1984).
29. Hedrick, S. M., Nielsen, E. A., Kavaler, J., Cohen, D. I., and Davis, M. M., Nature 308: 153-158 (1984).
30. Yamamoto, T., et al., Cell 39: 27-38 (1984).
31. Ullrich, A., et al., Nature 309: 418-425 (1984).
32. Wen, D., et al., Biochemistry 26: 4350-4357 (1987).
33. Radeke, M. J., Misko, T. P., Hsu, C., Herzenberg, L. A., and Shooter, E. M., Nature 325: 593-597 (1987).

34. Trent, C., Tsung, N., and Horvitz, H. R., Genetics 104: 619–647 (1983).
35. Ferguson, E. L., and Horvitz, H. R., Genetics 110: 17–72 (1985).
36. Folstein, S. E., et al., Science 229: 776–779 (1985).
37. Leonard, J. P., and Salpeter, M. M., J. Cell Biol. 82: 811–819 (1979).
38. Hogan, P. G., J. Neurosci. in press.
39. Choi, D. W., J. Neurosci. 7: 369–379 (1988).
40. Takumi, T., Ohkubo, H., and Nakanishi, S., Science 242: 1042–1045 (1988).
41. Murai, T., Kakizuka, A., Takumi, T., Ohkubo, H., and Nakanishi, S., Biochem. Biophys. Res. Commun. 161: 176–181 (1989).
42. Kang, J., Lemaire, H. G., Unterbeck, A., Salbaum, J. M., and Masters, C. L., Nature 325: 733–736 (1987).
43. McCusick, V. A., *Mendelian Inheritance in Man.* 7th edition, Johns Hopkins University Press, Baltimore (1989).
44. Dickson, D. W., et al., Acta Neuropathol. (Berl.) 71: 216–223 (1986).
45. Kohn, R., J. Neurol. Neurosurg. Psychiat. 34: 427–431 (1971).
46. Reif-Kohn, R., and Mundel, G., Confin. Neurol. 36: 23–32 (1974).
47. Duchen, L. W., and Strich, S. J., J. Neurol. Neurosurg. Psychiat. 31: 535–542 (1968).
48. Caddy, K. W. T., and Briscoe, T. J., Brain Res. 91: 276–280 (1975).
49. LaVail, M. M., Blanks, J. C., and Mullen, R. J., J. Comp. Neurol. 212: 217–230 (1982).
50. Pilar, G., and Landmesser, L., J. Cell Biol. 68: 339–356 (1976).
51. Chu-Wang, I. W., and Oppenheim, R. W., J. Comp. Neurol. 177: 33–58 (1978).
52. Knyihar, E., Csillik, B., and Rakic, P., Science 202: 1206–1209 (1978).
53. Cunningham, T. J., Int. Rev. Cytol. 74: 163–186 (1982).
54. Valverde, F., and Facal-Valverde, M. V., J. Comp. Neurol. 269: 168–192 (1988).
55. Chun, J. J. M., and Shatz, C. J., J. Comp. Neurol. 282: 555–569 (1989).
56. Way, J. C., and Chalfie, M., Cell 54: 5–16 (1988).
57. Hedgecock, E. M., Sulston, J. E. and Thomson, J. N., Science 22: 1277–279 (1983).
58. Chalfie, M., and Thomson, J. N., J. Cell Biol. 82: 278–289 (1979).
59. Ward, S., Thomson, N., White, J. G., and Brenner, S., J. Comp. Neurol. 160: 313–337 (1975).
60. White, J. G., Southgate, E., Thomson, J. N., and Brenner, S., Philos. Trans. Roy. Soc. Lond. (Biol.) 314: 1–340 (1986).
61. Emmons, S. C., Klass, M. R., and Hirsh, D., Proc. Natl. Acad. Sci. USA 76: 1333–1337 (1979).
62. Maniatis, T., Fritsch, E. F., and Sambrook, J., *Molecular Cloning: A Laboratory Manual,* Cold Spring Harbor Laboratory, New York (1982).
63. Ish-Horowicz, D., and Burke, J. F., Nucleic Acid. Res. 9: 2989–2998 (1981).
64. Fire, A., EMBO J. 5: 2673–2680 (1986).
65. Ozkaynak, E., and Putney, S. D., BioTechniques 5: 770–773 (1987).
66. Sanger, F., Nicklen, S., and Coulson, A. R., Proc. Natl. Acad. Sci. USA 74: 5463–5467 (1977).
67. Braunwald, E., Isselbacher, K., Petersdorf, R., Wilson, J., Martin, J., and Fauci, A., *Harrison's Principles of Internal Medicine,* McGraw-Hill Book Company, New York (1987).
68. Bowen, I. and Lockshin, R., eds., *Cell Death in Biology and Pathology,* Chapman and Hall Ltd., New York (1981).
69. Cowan, W. M., Fawcett, J., O'Leary, D., and Stanfield, B., Science 225: 1258–1265 (1984).
70. Potten, C., *Perspectives on Mammalian Cell Death,* Oxford University Press, Oxford (1987).
71. Walker, N., Harmon, B., Gobe, G., and Kerr, J., Meth. Achiev. Exp. Pathol. 13: 18–54 (1988).
72. Horvitz, R., Ellis, H., and Sternberg, P., Neurosci. Comment 1: 56–65 (1982).
73. Robertson, A., and Thomson, N., J. Embryol. Exp. Morph. 67: 89–100 (1982).
74. Hedgecock, E., Sulston, J., and Thomson, N., Science 220: 1277–1279 (1983).
75. Yuan, J., and Horvitz, H. R., Develop. Biol. 138: 33–41 (1990).

What is claimed is:

1. An isolated nucleic acid molecule encoding a wild-type *C. elegans* protein, wherein the *C. elegans* protein is encoded by the deg-1 gene which has the DNA sequence shown in FIG. 7 and, when mutated, is the genetic basis of neuronal degeneration associated with a neurodegenerative disorder.

2. An isolated nucleic acid molecule encoding a mutated *C. elegans* protein, wherein the mutated *C. elegans* protein is encoded by a mutated deg-1 gene which forms the genetic basis of neuronal degeneration associated with a neurodegenerative disorder.

3. A *Caenorhabditis elegans* strain containing an isolated nucleic acid molecule encoding a mutated *C. elegans* protein, wherein the mutated *C. elegans* protein is encoded by a mutant of the deg-1 gene designated u38, the deg-1 gene having the cDNA sequence shown in FIG. 7, with said strain designated TU38 and deposited with the ATCC under Accession No. 40818.

4. A *Caenorhabditis elegans* strain containing an isolated nucleic acid molecule encoding a mutated *C. elegans* protein, wherein the mutated *C. elegans* protein is encoded by a mutant of the deg-1 gene designated uIn1, the deg-1 gene having the cDNA sequence shown in FIG. 7, with said strain designated TU1191, and deposited with the ATCC under Accession No. 40817.

5. A *Caenorhabditis elegans* strain containing an isolated nucleic acid molecule encoding a mutated *C. elegans* protein, wherein the mutated *C. elegans* protein is encoded by a mutant of the mec-4 gene designated e1611, the mec-4 gene having the cDNA sequence shown in FIG. 9, with said strain designated CB1611, and deposited with the ATCC under Accession No. 40820.

6. A *Caenorhabditis elegans* strain containing an isolated nucleic acid molecule encoding a mutated *C. elegans* protein, wherein the mutated *C. elegans* protein is encoded by a mutant of the mec-4 gene designated u214, the mec-4 gene having the cDNA sequence shown in FIG. 9, with said strain designated TU214 and deposited with the ATCC under Accession No. 40819.

7. A *Caenorhabditis elegans* strain containing an isolated nucleic acid molecule encoding a mutated *C. elegans* protein, wherein the mutated *C. elegans* protein is encoded by a mutant of the mec-4 gene designated u231, the mec-4 gene having the cDNA sequence shown in FIG. 9, with said strain designated TU231 and deposited with the ATCC under Accession No. 40821.

* * * * *